US011179118B2

(12) United States Patent
Egolf et al.

(10) Patent No.: US 11,179,118 B2
(45) Date of Patent: *Nov. 23, 2021

(54) RADIATION SHIELD ASSEMBLY

(71) Applicant: Norad Designs LLC, Oviedo, FL (US)

(72) Inventors: John Barry Egolf, Oviedo, FL (US); Scott Pollak, Winter Park, FL (US)

(73) Assignee: Norad Designs LLC, Oviedo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/788,975

(22) Filed: Feb. 12, 2020

(65) Prior Publication Data

US 2020/0178915 A1   Jun. 11, 2020

Related U.S. Application Data

(63) Continuation of application No. 16/276,400, filed on Feb. 14, 2019, now Pat. No. 10,568,591.

(60) Provisional application No. 62/631,089, filed on Feb. 15, 2018, provisional application No. 62/693,140, filed on Jul. 2, 2018.

(51) Int. Cl.
*A61B 6/10* (2006.01)
*A61B 6/00* (2006.01)
*A61B 6/04* (2006.01)

(52) U.S. Cl.
CPC .............. *A61B 6/107* (2013.01); *A61B 6/44* (2013.01); *A61B 6/0407* (2013.01)

(58) Field of Classification Search
CPC .......... A61B 6/107; A61B 6/44; A61B 6/0407
See application file for complete search history.

(56) References Cited

U.S. PATENT DOCUMENTS

| | | |
|---|---|---|
| 3,944,838 A | 3/1976 | Gade |
| 5,006,718 A | 4/1991 | Lenhart |
| 5,090,044 A | 2/1992 | Kobayashi |
| 6,090,044 A | 7/2000 | Bishop et al. |
| 10,568,591 B2 * | 2/2020 | Egolf .................. A61B 6/44 |
| 2006/0076522 A1 | 4/2006 | Goldstein |
| 2014/0048730 A1 | 2/2014 | Niedzielski et al. |
| 2018/0220977 A1 | 8/2018 | Colling |

OTHER PUBLICATIONS

International Search Report and Written Opinion of the International Searching Authority dated May 6, 2019, 14 pages.
Non-Final Office Action on U.S. Appl. No. 16/276,400 dated Jun. 27, 2019.

(Continued)

*Primary Examiner* — Nicole M Ippolito
*Assistant Examiner* — Hanway Chang
(74) *Attorney, Agent, or Firm* — Foley & Lardner LLP

(57) ABSTRACT

A radiation shield assembly includes a shield configured to block radiation and a rail assembly configured to position the shield in between the radiation table and a radiation source. The shield is movable between a retracted position and an extended position along a length of the rail assembly. In the extended position, the shield extends along a portion of a radiation table and blocks radiation from the radiation source to the portion of the radiation table. In the retracted position, the shield exposes at least some of the portion of the radiation table to the radiation.

20 Claims, 15 Drawing Sheets

(56) References Cited

OTHER PUBLICATIONS

Notice of Allowance on U.S. Appl. No. 16/276,400 dated Oct. 30, 2019.
International Preliminary Report on Patentability received in International Application No. PCT/US2019/018087 dated Aug. 27, 2020, 6 pages.

* cited by examiner

RADIATION SHIELD ASSEMBLY

CROSS-REFERENCE TO RELATED PATENT APPLICATIONS

This application is a continuation of, and claims priority to co-pending U.S. patent application Ser. No. 16/276,400 filed Feb. 14, 2019 which claims priority to and the benefit of U.S. Provisional Patent Application No. 62/631,089 filed Feb. 15, 2018, and U.S. Provisional Patent Application No. 62/693,140 filed Jul. 2, 2018, the contents of all of which are incorporated herein by reference in their entireties.

FIELD

This disclosure relates generally to radiation shield assemblies.

BACKGROUND

Radiation exposure is detrimental to human health. For example, a comprehensive review of available biologic and biophysical data supports a "no-threshold" risk model for radiation exposure since the risk of cancer may increase linearly at low doses of radiation without a threshold. The dose of radiation has the potential to cause a small increased risk of malignancy in humans. (National Research Council. *Health Risks from Exposure to Low Levels of Ionizing Radiation: BEIR VII Phase* 2. Washington, D.C.: National Academies, 2006.)

For example, within the survivors of the Hiroshima and Nagasaki atomic bombings, which represents a large population that includes all ages and both sexes, more than 60% of exposed survivors received a dose of radiation of less than 100 mSv (the definition of low dose used by the BEIR VII report). (National Research Council, 2006.) The Radiation Effects Research Foundation (RERF) in Japan has conducted follow-up studies on these survivors for more than 50 years to evaluate the health effects of ionizing radiation. From these studies, it was found that the occurrence of solid cancers increases in proportion to radiation dose. (Preston D L, Ron E, Tokuoka S, et al. *Solid cancer incidence in atomic bomb survivors:* 1958-1998. Radiat Res, 2007; 168: 1-64., Cullings H M, Fujita S, Funamoto S, et al. *Dose estimation for atomic bomb survivor studies: Its evolution and present status*. Radat Res, 2006; 166: 219-54.) See also, Sanchez R., Vano E, Fernandez J M, Gallejo J J. *Staff radiation doses in real-time display inside the angiography room*. Cardiovasc Intervent Radiol, 2010.

However, many different medical radiologic procedures or examinations, such as electrophysiological procedures, cardiac catheterization, angioplasty, cardiac stenting, cardiac valve procedures, and orthopedic procedures require the use of radiation. Although many different technologies attempt to avoid or minimize radiation during these procedures, there is still a moderate to high x-ray exposure as evidenced by reported fluoroscopy in numerous studies. (Cano O, Alonso P, Osca J, et al. *Initial experience with a new image integration module designed for reducing radiation exposure during electrophysiological ablation procedures*. J Cardiovasc Electrophysial, 2015; 26: 662-670., Valderrabano M, Greenberg S, Razavi H, et al. *3D cardiovascular navigation system: accuracy and reduction in radiation exposure in left ventricular lead implant*. J Cardiovasc Electrophysiol, 2014; 25: 87-93.) Implant procedures may incur a higher exposure to the practitioner since the x-ray generator may be closer to the practitioner.

Some technology allows real-time assessment of radiation dose exposure at a given location. In radiation protection dosimetry, two types of dosimeters may be used: passive and active (direct reading). Passive dosimeters, such as film badges, may integrate the radiation dose over the measurement period. Active electronic dosimeters may combine a detector with the readout to display the radiation dose value (e.g., the rate of radiation exposure). (Ankerhold U, Hupe O, Ambrosi P. *Deficiencies of active electronic radiation protection dosimeters in pulsed fields*. Oxford University Press, 2009; 135:149-153.) Real-time radiation dose feedback utilizing dosimeters have been shown to reduce radiation exposure to the practitioners. (Racadio J, Nachabe R, Carelson B, et al. *Effect of real-time radiation dose feedback on pediatric interventional radiology stop radiation exposure*. Journal of Vascular and Interventional Radiology, 2013; 25:119-126.)

During a radiologic procedure, a radiation source, such as an x-ray tube below the table holding the patient, may emit radiation (e.g., x-rays) as a direct radiation beam toward an area of the patient's body that is intended to be examined. Most of the direct radiation beam enters into the patient in order to allow the patient to be examined and subsequently exits the patient's body. The area of the patient's body that is under examination receives some radiation due to the direct radiation beam. The entrance radiation dose is the amount of radiation that enters into the patient and the exit radiation dose is the amount of radiation that exits from the patient.

However, radiation from the direct radiation beam deflects, which causes the radiation to scatter and forms "scatter radiation." Scatter radiation refers to any radiation that is outside of the direct radiation beam. A portion of the radiation may scatter before and/or after the radiation enters into and exits from the patient's body. Some of the scatter radiation enters into areas of the patient's body that are not under examination. Accordingly, these areas of the patient's body not under examination also are exposed to and receive radiation due to the scatter radiation, which needlessly increases the patient's overall exposure to radiation (i.e., the exit radiation dose) and also increases the amount radiation exiting the patient (i.e., the exit radiation dose), which affects the practitioners.

The practitioners are also exposed to the scatter radiation, both the scatter radiation that has not entered the patient's body and the scatter radiation that has entered and exited the patient's body. The scatter radiation from areas of the patient's body that are not under examination, in particular, needlessly increases the amount of radiation that the practitioners are exposed to.

In order to reduce the amount of radiation that the practitioners are exposed to (specifically due to the radiation exiting the patient), lead skirts that are attached to the side of the x-ray table, mobile seals, suspended plexiglass shields, and sterile pads placed on top of or above the patient may be used. Most of these devices are on the top of the examining table and are only designed to shield the practitioners from the radiation exiting the patient. These devices do not protect the patient from excessive radiation (e.g., scatter radiation) entering into areas of the patient's body not under examination and instead allow the patient to be needlessly exposed to the scatter radiation. Furthermore, the shielding above the patient on top of the examining table may lack symmetry in placement, which may create gaps in protection to the practitioners. Even further, it may be difficult to move shielding that is positioned on top of the procedure table in order to visualize different portions of the patient's body.

Therefore, certain procedures, such as cardiac catheterization, expose areas of the patient's body that do not need to be visualized to radiation, which may needlessly increase both the patient's and the practitioner's overall radiation exposure.

SUMMARY

Various embodiments provide for a radiation shield assembly that includes a shield configured to block radiation and a rail assembly configured to position the shield in between the radiation table and a radiation source. The shield is movable between a retracted position and an extended position along a length of the rail assembly. In the extended position, the shield extends along a portion of a radiation table and blocks radiation from the radiation source to the portion of the radiation table. In the retracted position, the shield exposes at least some of the portion of the radiation table to the radiation.

These and other features (including, but not limited to, retaining features and/or viewing features), together with the organization and manner of operation thereof, will become apparent from the following detailed description when taken in conjunction with the accompanying drawings, wherein like elements have like numerals throughout the several drawings described below.

DETAILED DESCRIPTION

Referring generally to the figures, disclosed herein is a radiation shield assembly, as shown according to exemplary embodiments, that may be used to protect the patient and the practitioners and reduce their exposure to ionizing radiation during radiology procedures. The radiation shield assembly may minimize, reduce, block, or stop portions of the radiation from entering the patient, which protects both the patient and the practitioners, minimizes their overall exposure to radiation, and avoids penetration of radiation into the patient's body in areas not directly involved in the imaging field and not intended to be examined. The radiation shield assembly still allows other portions of the radiation to enter into certain areas of the patient's body to allow these areas to be examined through radiation. Due to the potential health consequences of radiation exposure, it is highly beneficial to use the radiation shield assembly to reduce or block radiation exposure to organic material.

Radiation Shield Assembly

Figure 1:
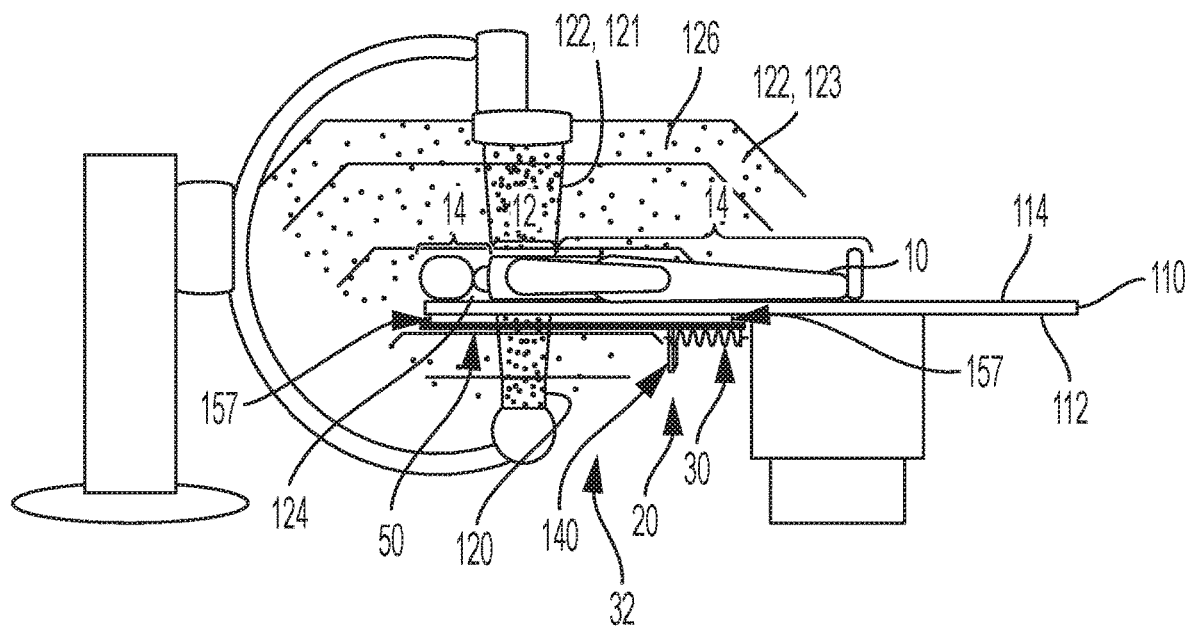
FIG. 1 is a schematic, side view of a radiation shield assembly on an examination table and in a retracted position according to one embodiment.
Figure 2:
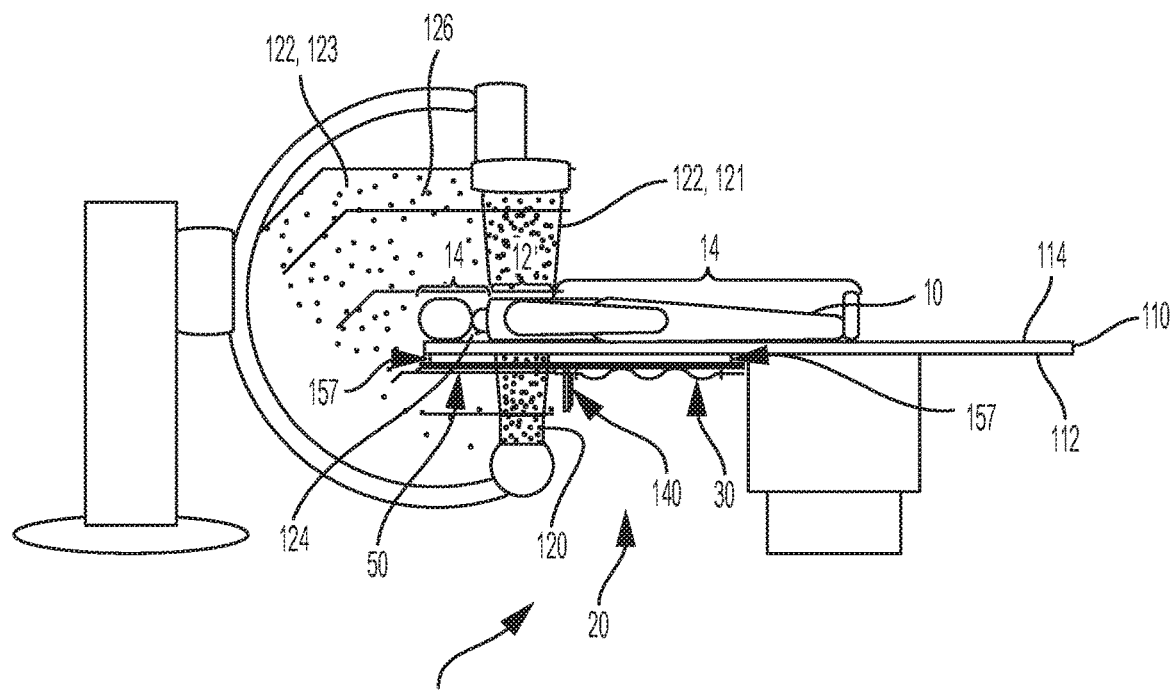
FIG. 2 is a schematic, side view of the radiation shield assembly of FIG. 1 in a partially extended position.

As shown in FIGS. 1-2, the patient 10 may lay on the procedure, radiology, or examining table 110 during a radiology procedure. The table 110 may, for example, have an upper surface formed from clear plexiglass, carbon fiber, or other material that does not materially affect emitted radiation. The radiation source 120 may be positioned underneath the table 110 and emit radiation 122 (e.g., x-rays) from underneath the table 110. Accordingly, the radiation 122 moves through the table 110 and toward an examination area 12 of the patient's body. The examination area 12 refers to the area of the patient's body to be examined and therefore to be exposed to radiation 122. The rest of the patient's body that is not intended to be examined (and therefore does not need to be exposed to radiation) is referred to as the nonexamination area 14 of the patient 10.

The radiation source 120 emits radiation 122 that comprises both a direct radiation beam 121 and the scatter radiation 123. The active or direct radiation beam 121 refers to radiation that is aimed toward the examination area 12 of the patient's body. The scatter radiation 123 refers to radiation that is deflected off of matter and accordingly is outside of the direct radiation beam 121 and may enter into nonexamination areas 14 of the patient's body without the radiation shield assembly 20, as described further herein. The entrance radiation dose 124 is the amount of radiation 122 that enters into the patient 10, and the exit radiation dose 126 is the amount of radiation 122 that exits from the patient 10.

In order to expose the examination area 12 of the patient 10 to radiation 122 and thereby allow the examination area 12 to be examined, the radiation source 120 emits radiation 122 as the direct radiation beam 121 aimed toward the examination area 12 of the patient's body. Some of the radiation 122 successfully exposes the examination area 12 to radiation. However, as shown in FIGS. 1-2, some of the radiation 122 is deflected outside of the direct radiation beam 121 and instead is emitted as scatter radiation 123. Without the radiation shield assembly 20 (or when the shield 30 of the radiation shield assembly 20 is retracted (i.e., in the retracted position 32), as shown in FIG. 1), the scatter radiation 123 may be directed to a variety of different areas of the patient's body, including the nonexamination area 14 of the patient 10.

When the shield 30 of the radiation shield assembly 20 is at least partially extended (i.e., the partially extended position 34, as shown in FIG. 2 (compared to FIG. 1) and as described further herein), the radiation shield assembly 20 protects at least a portion of the patient 10 (and the practitioners (e.g., the doctors, physicians, medical staff, and operators) that are nearby the patient 10) from excessive and unnecessary exposure to radiation by selectively blocking or preventing some of the radiation 122 (in particular, the scatter radiation 123) from unnecessarily entering into certain areas of the patient's body (i.e., into at least a portion of the (or the entire) the nonexamination area(s) 14). The radiation shield assembly 20 still, however, allows some of the radiation 122 (i.e., at least a portion of the direct radiation beam 121) to enter into other areas of the patient's body (i.e., into the examination area 12) through areas of the table 110 that the shield 30 does not extend along.

Accordingly, the radiation shield assembly 20 significantly reduces the overall amount of radiation exposure to both the patient 10 and the practitioners. More specifically, the radiation shield assembly 20 reduces the patient's overall amount of radiation exposure by preventing radiation 122 from entering into the nonexamination area 14 of the patient 10, which reduces the amount of entrance radiation dose 124 to the patient 10. In turn, by reducing the amount of entrance radiation dose 124 to the patient 10, the amount of exit radiation dose 126 from the patient 10 is reduced, which thus reduces the practitioners' exposure to radiation. The radiation shield assembly 20 may reduce radiation exposure by 55-99% in certain locations.

The majority of the radiation shield assembly 20 is positioned underneath the table 110 (where the patient is positioned on top of the table 110). Accordingly, the radiation shield assembly 20 may have a low profile underneath the table 110 in order to not be obtrusive and to minimize interference with the radiation system in extreme angles. Furthermore, the various components of the radiation shield assembly 20 can be sized according to any particular size of the table 110 to be used such that the radiation shield assembly 20 can be used with a wide range of sizes of tables 110. The various components of the radiation shield assembly 20 can also be sized to accommodate specialized equipment, procedures, or needs.

It is understood that the radiation shield assembly 20 may be used with a variety of different types of procedures to visualize hard and/or soft tissue, including but not limited to percutaneous radiologic procedures and with different types of radiation 122, including but not limited to x-rays.

Figure 3:
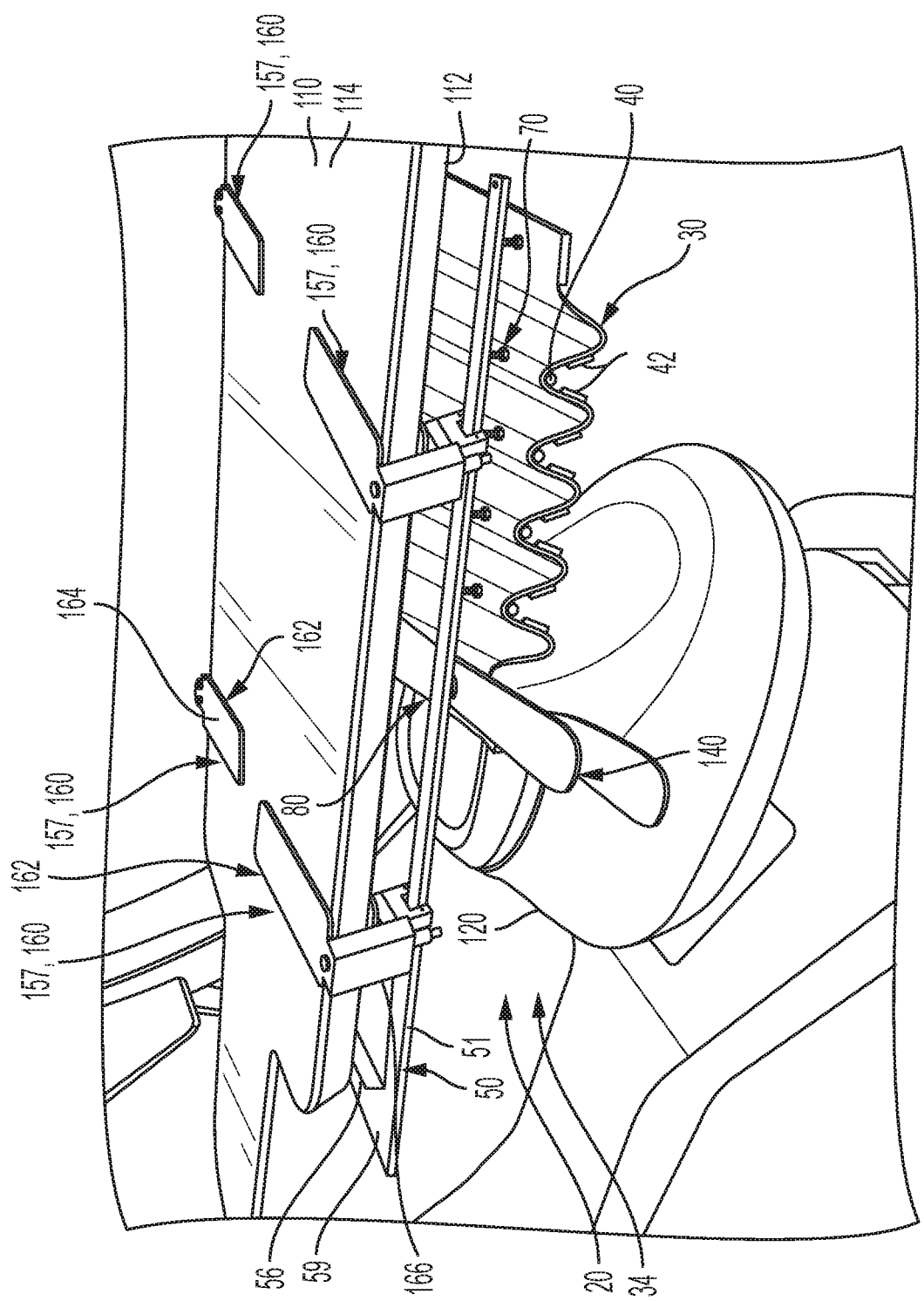
FIG. 3 is a perspective view of a radiation shield assembly attached to a table according to one embodiment.
Figure 4:
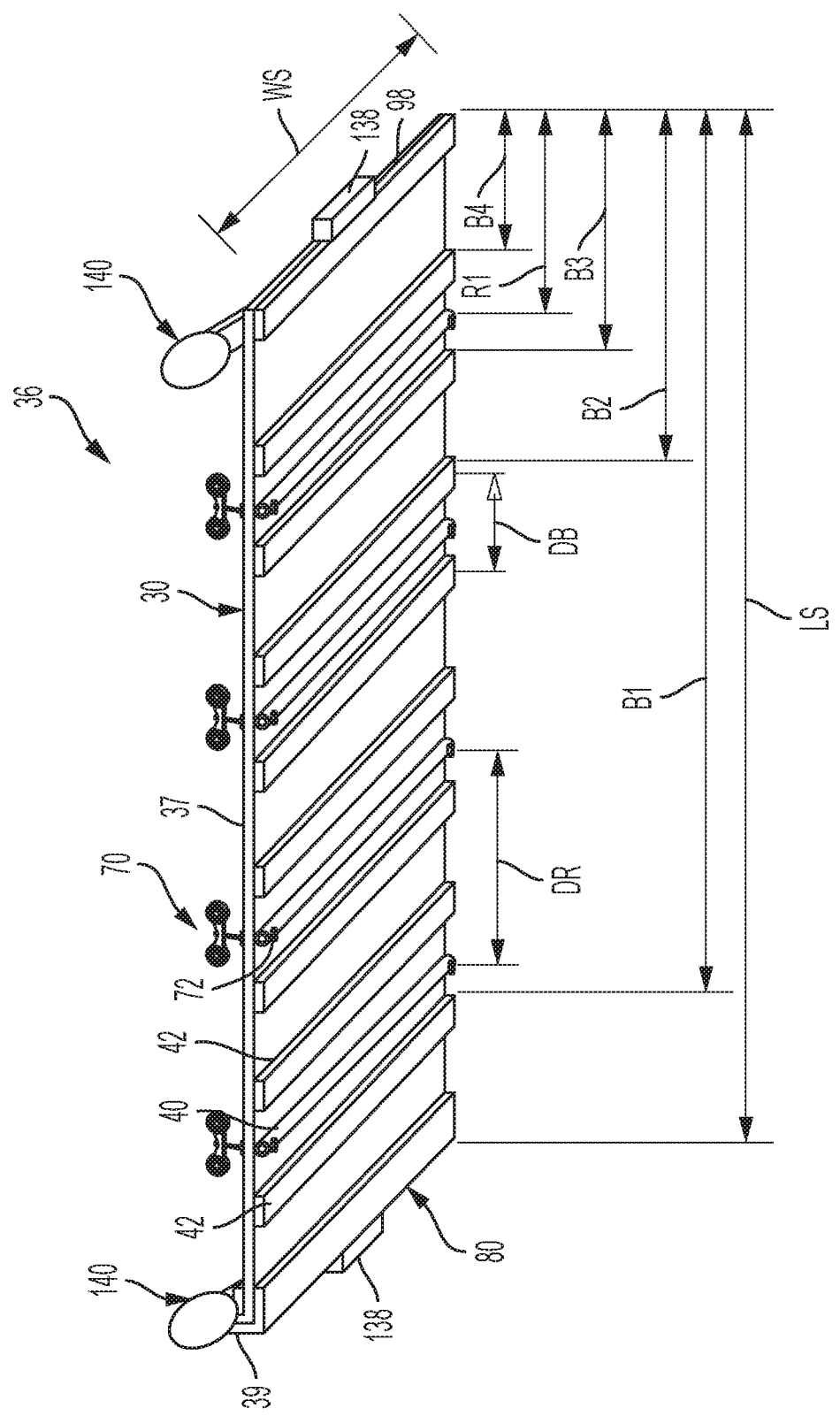
FIG. 4 is perspective view of a shield (in an extended position) and locking handles of the radiation shield assembly of FIG. 3.
Figure 5A:
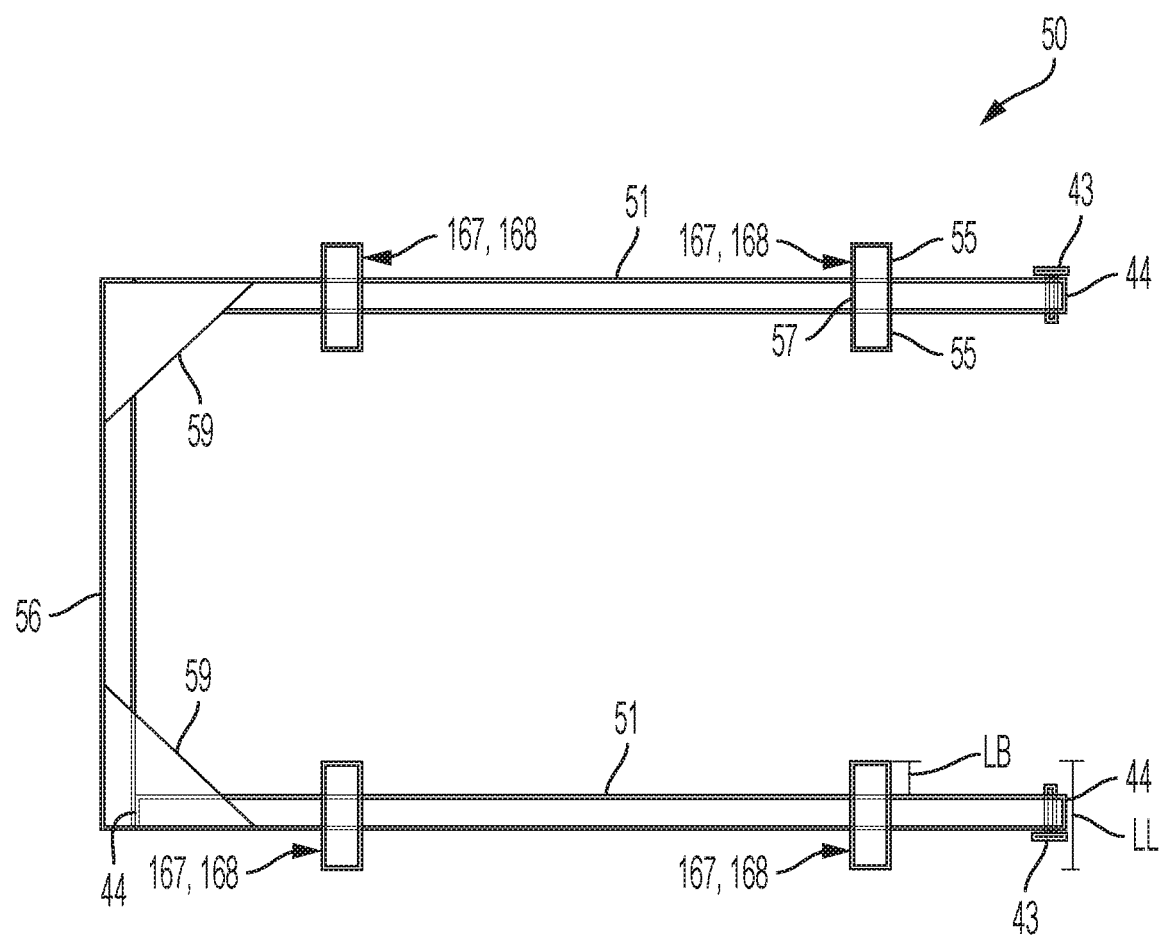
FIG. 5A is a top, partially transparent view of a rail assembly of the radiation shield assembly of FIG. 3.

As described further herein, the radiation shield assembly 20 comprises a shield 30 to block the radiation 122 and to protect the patient 10 and the practitioner(s) (as shown in FIG. 4), a plurality of shield supports (i.e., rods 40 and bars 42) to support and fold the shield 30 (as shown in FIG. 4), and a rail assembly 50 (as shown in FIG. 5A) that the shield 30 can be moved along and supported by and that is configured to position the shield 30 in between the table 110 and the radiation source 120. As shown in FIG. 3, the shield 30, the rods 40, the bars 42, and the rail assembly 50 are all positioned underneath the table 110 (and above the radiation source 120, thereby between the table 110 and the radiation source 120). Accordingly, the shield 30 is positioned between the rods 40 and bars 42 and the rail assembly 50 (with the rods 40 and the bars 42 positioned beneath the shield 30 and the rail assembly 50 positioned above the shield 30). The rail assembly 50 is positioned between the shield 30 and the bottom surface 112 of the table 110. The rods 40 and the bars 42 are position between the bottom surface of the shield 30 and the radiation source 120. As shown in subsequent figures and described further herein, the radiation shield assembly 20 further comprises a plurality of shield adjusters 70 to move the shield 30 along the length of the rail assembly 50, a deflector 80 to position the end of the shield 30 further shield the patient 10 and the practitioners, at least one locking mechanism (i.e. a locking handle 140) to control and lock the position of the shield 30 along the length of the rail assembly 50, and at least one table mount 157 (i.e., a suction mount 60 and/or a clamp mount 160) to removably and reattachably attach the radiation shield assembly 20 (in particular the rail assembly 50) to the table 110.

The radiation shield assembly 20 can be easily produced and assembled together through several small prefabrication steps attaching, for example only, the shield 30, the rods 40, the bars 42, and the rail assembly 50. Accordingly, the radiation shield assembly 20 does not require a large-scale facility or complex machinery for production or assembly. Most of the radiation shield assembly 20 may be independently manufactured and later assembled The various materials within the radiation shield assembly 20 are used to minimize the weight of the radiation shield assembly 20 and to prevent corrosion since the radiation shield assembly 20 will be used around and with various cleaning detergents and saline solutions.

The Shield

The shield 30 is configured to block radiation 122 (in particular the radiation 122 from the radiation source 120). The shield 30 is positioned in between the table 110 and the radiation source 120 (in particular below the table 110 and above the radiation source 120) in order to prevent radiation 122 from moving through the table 110 and thus into the patient 10 (who is on top of the table 110).

As shown in FIGS. 1-3, the curtain, shutter, or shield 30 (as shown in FIG. 4) may be dynamically and easily moved or adjusted in either direction along at least a portion of the underside of the table 110 (i.e., along at least a portion of the length of the rail assembly 50) before and/or during a procedure in order to provide the desired amount and location of shielding from radiation 122 to the patient 10 and to accommodate different radiation views of the patient 10. Accordingly, the shield 30 protects the areas of the patient's body that are not being visualized or examined (i.e., the nonexamination area(s) 14) from radiation 122 and thereby reduces the overall amount of radiation 122 traveling through the patient 10 and to the practitioners.

The practitioner may easily move the shield 30 according to the desired position beneath the patient 10 and along the table 110 in order to provide more or less radiation shielding to the patient 10 and to change where the patient 10 is exposed to radiation and where the patient 10 is shielded from radiation. For example, the shield 30 can be expanded, moved, or contracted over a specific surface area between a retracted position 32 (as shown in FIG. 1), a partially extended position 34 (as shown in FIGS. 2-3), and an extended position 36 (as shown in FIG. 4) along a length of the rail assembly 50. In the extended position 36 (as well as the partially extended position 34), the shield 30 extends along a portion of the table 110 and thus blocks radiation 122 from the radiation source 120 to that portion of the table 110. Due to the material of the shield 30, the shield 30 provides shielding and protection regardless as to whether the shield 30 is completely folded, partially folded or extended, or completely extended. However, by moving the shield 30 between the positions, the shield 30 can accommodate and provide protection with a variety of different views and angles of radiation 122, and the amount and position of shielding is changed.

In the retracted position 32 (as shown in FIG. 1), the shield 30 is completely folded and out of the way of the path of radiation 122. Accordingly, in the retracted position 32, the shield 30 exposes at least a portion of the table 110 (and thus the patient 10) to the radiation 122. Depending on the position of the folded shield 30 relative to the patient 10, the shield 30 may allow the entire patient 10 (i.e., both the examination area 12 and the nonexamination area 14) (and the majority of the table 110) to be completely exposed to the radiation 122 in the retracted position 32 and does not restrict any radiation 122 from moving through the table 110 and entering into the patient 10.

In the partially retracted position or the partially extended position 34 (as shown in FIG. 2), the shield 30 is both partially retracted and partially extended, thus only covering and shielding certain areas of the patient 10 from radiation 122 for protection and exposing other areas of the patient 10 to radiation 122 for examination (and thus also shielding certain portions of the table 110 to radiation 122 and exposing other areas of the table 110 to radiation 122). The shield 30 may still be partially folded since the shield 30 is not completely extended along the length of the rail assembly 50. In the partially extended position 34, both longitudinal edges or ends of the shield 30 can be moved to anywhere along the length of the rail assembly 50 (and thus, along at least a portion of the length of the patient 10 and the table 110) in order to select which areas of the patient 10 (and the table 110) are shielded from radiation 122. Accordingly, the shield 30 can be positioned such that the shield 30 does not interfere with the field of view of the examination area 12 of the patient 10. Optionally, the end of the shield 30 can be positioned at or extend up to the edge of the direct radiation beam 121 (as shown in FIG. 2), thus protecting the nonexamination areas 14 of the patient 10 from any scatter radiation 123 that is outside of the direct radiation beam 121.

In the extended position 36 (as shown in FIG. 4), the shield 30 is fully extended along the rail assembly 50 and a portion of the table 110 and is not folded at all and/or is extending along the entire usable length of the rail assembly 50. The shield 30 blocks radiation 122 from the radiation source 120 to this portion of the table 110 (and thus any portion of the patient 10 extending within this portion of the table 110). Depending on the size of the shield 30 and the rail assembly 50 and the size and position of the patient 10, the patient's entire body may be completely protected from the radiation 122 when the shield 30 is in the extended position 36. In the extended position 36, the shield 30 is substantially horizontal.

Since the entire shield 30 is movable along the length of the rail assembly 50 and the length of the rail assembly 50 extends along at least a portion of the table 110, the shield 30 can be moved to shield any portion of the table 110 (and thus the patient 10) from radiation 122 and thus can protect any portion of the patient's body (while exposing other portions of the patient 10 (and thus the table 110) to radiation 122 for the procedure). For example, the shield 30 may protect either the upper body or the lower body (and thus allow the other of the upper body or lower body to be exposed to radiation 122 for examination) by extending along the top or bottom of the table 110. As a further example, the shield 30 may be moved to cover the thoracic area of the patient 10 (while exposing other portions of the patient's body), allowing the practitioner to perform peripheral vascular procedures without visual impedance from the shield 30. Alternatively, the shield 30 may be moved to cover at least the lower half of the patient 10 (and thus expose the upper half of the patient 10) to allow the practitioner to perform thoracic or cardiac procedures (as shown in FIG. 2, for example). If only the heart needs to be visualized, the shield 30 may be positioned to cover all other areas of the body, such as the rest of the torso, (while exposing the heart) to minimize the patient's exposure to radiation.

Alternatively or additionally, the shield 30 may be positioned along the middle of the length of the rail assembly 50 in order only cover a middle portion of the patient's body (and the table 110). Accordingly, with such an arrangement, an upper portion and a lower portion of the patient's body (and thus the table 110) may both be exposed to radiation 122 for examination purposes while a middle portion of the patient's body (and the table 110) is protected from radiation 122.

According to one embodiment, the radiation shield assembly 20 may include multiple shields 30 along the length of the rail assembly 50. For example, the radiation shield assembly 20 may include two shields 30. Accordingly, either or both of the shields 30 can be adjusted to protect and shield at least a portion of the top and bottom portions of the patient's body (and the table 110) from the radiation 122 while allowing a middle portion of the patient's body (and the table 110) to be exposed to the radiation 122.

As shown in FIGS. 1-3, preferably the entire shield 30 (as well as the rail assembly 50 and the majority of the rest of the radiation shield assembly 20) is positioned underneath the table 110 (e.g., along a bottom surface 112 of the table 110). The patient 10 may lay on the topside or top side or surface 114 of the table 110, which is directly opposite the underside or bottom side or surface 112 of the table 110. By positioning the shield 30 under the table 110 (and under the patient 10), the shield 30 protects both the patient 10 and the practitioners by preventing scatter radiation 123 from entering into the patient 10 (comparatively, if the shield were above the table 110 and the patient 10, the patient 10 would not be protected from the scatter radiation 123). Additionally, since the shield 30 is below the table 110, the shield 30 is more easily adjusted (compared to if the shield 30 were above the table 110), even while the patient 10 is on top of or being held by the table 110. Therefore, the shield 30 can be moved and adjusted to various positions (i.e., between the retracted position 32 and the extended position 36 (and any position therebetween)) while the patient 10 is laying on the table 110 and during the procedure, without moving or disturbing the patient 10 or compromising sterile areas on the top surface 114 of the table 110 where the practitioner can access the patient 10. Furthermore, positioning the shield 30 underneath the table 110 and patient 10 allows for more symmetrical shielding (compared to a shield above the patient), which allows the radiation shield assembly 20 to block the radiation 122 more predictably.

As shown in FIG. 4, the shield 30 includes a body 37 and may optionally further include at least one vertical portion or angled end 39. The body 37 extends substantially parallel to the table 110 and horizontally when the shield 30 is in the extended position 36 (i.e., when the shield 30 is completely unfolded). Further, the body 37 is configured to be folded when the shield is in the retracted position 32 or the partially extended position 34. The body 37 makes up the majority of the shield 30 (compared to the angled end 39).

The angled end 39 is positioned along a longitudinal end of the body 37 (optionally the shield 30 may include two angled ends 39 positioned along opposite longitudinal ends of the body 37). The angled end 39 extends substantially perpendicular from the body 37 when the shield 30 is in the extended position 36 and to the bottom surface 112 of the table 110. The angled end 39 may not be, however, folded when the shield is in the retracted position 32 or the partially extended position 34. As described further herein, the angled end 39 provides additional shielding and prevents radiation 122 from moving into an area between the top surface of the body 37 of the shield 30 and the bottom surface 112 of the table 110. Accordingly, the top of the angled end 39 may directly abut the bottom surface 112 of the table 110.

Figure 10:
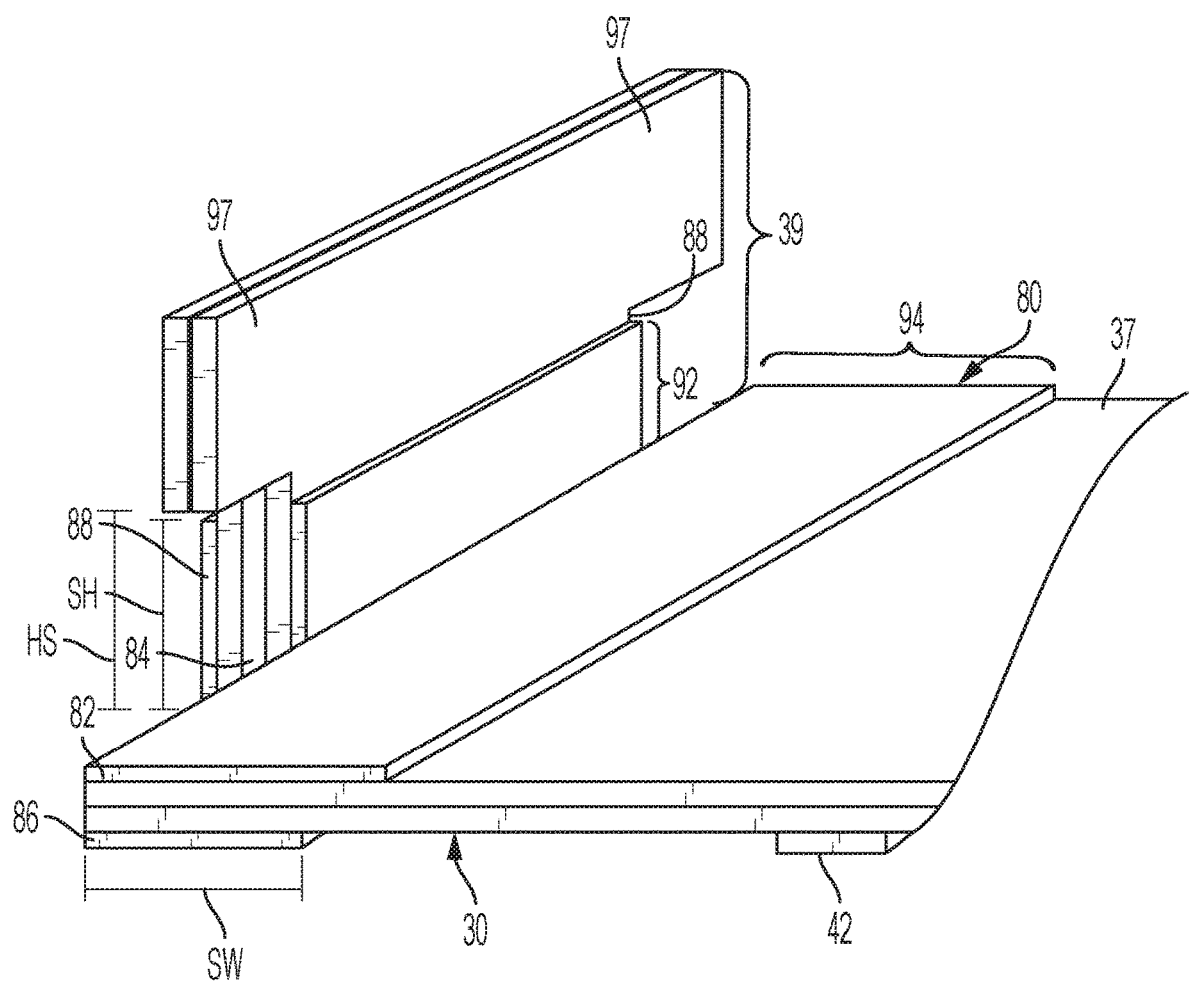
FIG. 10 is a perspective view of a deflector and a portion of the shield of FIG. 3.

Furthermore, as shown in FIG. 10 and as described further herein, the angled end 39 may include at least one flap 97 along at least one side (in the width direction of the shield 30). The angled end 39 may include two flaps 97 on opposite sides of the angled end 39 along the width direction of the shield 30. The flap 97 is disconnected (with, for example, a cut or slit) along a bottom edge of the flap 97 from the rest of the angled end 39 or the body 37 such that the flap 97 can move independently in the direction of movement of the shield 30 along the rail assembly 50 relative to the rest of the angled end 39 and the body 37. In other words, the angled end 39 is partially disconnected from the body 37 along opposite sides along the width of the shield 30. Since the angled end 39 may extend higher than the mount supports 167, the flaps 97 allow the angled end 39 to move past any mount supports 167 (in the direction of movement of the shield 30) that extend inwardly from the rails 51 of the rail assembly 50 and are above the body 37 of the shield 30 (as well as any table mounts 157) while the shield 30 moves along the length of the rails 51.

The angled end 39 may also include at least one indentation or notch 88 (along a lower portion of the angled end 39) that separates the bottom edge of the flaps 97 from the rest of the angled end 39 or the body 37. Accordingly, the notch 88 is positioned between the flap 97 and the body 37 of the shield 30. The shield 30 is wider along the flap(s) 97 and the body 37 of the shield 30 (to maximize how much radiation 122 is blocked) than along the notch(es) 88. Since the notches 88 are less wide than the flaps 97 and the body 37 (and the angled end 39 extends above the body 37, toward the rail assembly 50 and the mount supports 167), the notches 88 provide clearance to allow the angled end 39 of the shield 30 to easily move past the mount supports 167 and any table mounts 157 while the shield 30 moves along the length of the rails 51.

The shield 30 may be constructed out of a variety of different radiation-blocking, radiopaque materials that block or attenuate radiation 122, rather than allowing radiation to pass through. For example, the shield 30 may be a conventional flexible lead and/or aluminum shield that is radiopaque (and thus blocks or attenuates radiation 122) and is flexible. The shield 30 may be or may include lead impregnated polymer and/or polyurethane. As shown in FIG. 10, the shield 30 may include two layers or plys of lead or aluminum.

Optionally, the shield 30 may include a covering, such as a non-ripped nylon covering or a vinyl covering, on one or both sides of the radiation-blocking material of the shield 30. The covering may be in a variety of different colors. The covering may allow the shield 30 to be non-permeable (to blood, for example) and easily cleaned and wiped down (with an anti-microbial cleaning agent, for example).

In order to provide adequate radiation shielding to the patient, the shield 30 may be approximately the same width (or alternatively more or less wide) than the table 110.

According to one embodiment as shown in FIG. 4, the width WS of the shield 30 may be approximately 10-30 inches and the length LS of the shield 30 may be approximately 20-40 inches. According to another embodiment, the width WS of the shield 30 may be approximately 15-25 inches and the length LS of the shield 30 may be approximately 25-35 inches. According to one embodiment, the width WS of the shield 30 may be approximately 18 inches and the length LS of the shield 30 may be approximately 28-30 inches. However, it is understood that the width WS and/or the length LS of the shield 30 may be larger or smaller.

The horizontal length LS of the shield 30 may be slightly less than the length of the rails 51 of the rail assembly 50 (along the direction that the shield 30 is movable) in order to allow the shield 30 to be completely extended into the extended position 36. Accordingly, the end of the shield 30 may be spaced from the end of the rails 51 when the shield 30 is in the extended position 36.

The thickness of the shield 30 may be sufficiently thick to completely block radiation 122. According to one embodiment, the shield 30 may be approximately 0.0001-0.1 inches thick, more preferably 0.001-0.04 inches (0.25-1 mm) thick, or most preferably 0.02 inches (0.5 mm) thick. However, it is understood that a thicker shield 30 may be used to further block the radiation 122.

The Rods and the Bars

As shown in FIG. 4, the plurality of shield supports of the radiation shield assembly 20 provide support and structure for the shield 30, fold the shield 30 in the partially extended position 34 and the retracted position 32, and may further block radiation 122 (in addition to the shield 30). The plurality of shield supports comprises at least one rod 40 and at least one bar 42. Multiple rods 40 and bars 42 may be attached to the shield 30 and positioned next to each other along the length of the shield 30 (in the direction that the shield 30 is movable between the retracted position 32 and the extended position 36). The rods 40, the bars 42, and the shield 30 move with each other along the length of the rail assembly 50 (as the shield 30 is being moved between the retracted position 32 and the extended position 36) to expose certain areas of the patient's body while covering or protecting other areas of the patient's body.

As shown in FIG. 4, the rods 40 and the bars 42 may be partially alternately positioned next to each other along the length of the shield 30 in order to protect and support the shield 30 (in particular along its width) and allow the shield 30 to fold or accordion in a particular manner. For example, each rod 40 (aside from any rod 40 on the end) may be surrounded on either side by two bars 42. Each bar 42 (aside from any bars 42 on the end) may be surrounded on either side by one other bar 42 and one rod 40. The radiation shield assembly 20 may include any number and arrangement of rods 40 and bars 42. For example, according to one embodiment as shown in FIG. 4, the radiation shield assembly 20 may include four rods 40 and eight bars 42. According to another embodiment, the radiation shield assembly 20 may include six rods 40 and ten bars 42 and may be positioned such that two bars 42 are positioned between each of the rods 40 to help properly fold the and support the shield 30. According to another embodiment, the radiation shield assembly may include six rods 40 and nine bars 42. The number of rods 40 and bars 42 supporting the shield 30 may depend on the length of the shield 30 and the desired number and size of folds when the shield 30 is in the retracted position 32 or partially extended position 34.

Furthermore, as shown in FIG. 3, the rods 40 and the bars 42 are configured to cause the shield to fold or accordion together into an accordion-type fold (when the shield 30 is in the retracted position 32 or the partially extended position 34) in order to allow certain areas of the patient's body to be exposed to the radiation 122 while protecting other areas of the patient's body from radiation 122. The rods 40 and the bars 42 create natural folds in the shield 30 (without sharp edges) to prevent the shield 30 from drooping or ripping and to maintain the integrity of the shield 30. The accordion fold may also allow the shield 30 to be stored or retracted in a compact manner in the retracted position 32 to allow the practitioner to completely view the entire body of the patient 10 if desired.

Substantially round rods 40 may be used in order to allow the shield 30 to be folded without any sharp corners (in particular along the top crease line or fold of the shield 30), which prevents the lead impregnated polymer of the shield 30 from cracking or being cut by the rods 40 (as shown in FIG. 3). Otherwise, if the lead impregnated polymer of the shield 30 is folded over a sharp corner, the shield 30 may develop a linear crack (along the width of the shield 30, for example), which may fatigue the shield 30 over time and reduce how much radiation 122 is blocked by the shield 30. As described further herein, the rods 40 attach the shield 30 to the rail assembly 50 (through the shield adjusters 70) and accordingly are located along the top portion or bend of each of the folds. The rods 40 may have a substantially circular cross-section or may have rounded corner or edges, depending on the desired configuration. The rods 40 may optionally be hollow or at least partially solid along their length. According to one embodiment, there may be no rods (or bars) positioned along the bottom portion or bend of each of the folds, as shown in FIG. 3, which correspond to an area that two bars 42 are next to each other along the length of the shield 30 (with no rod 40 in between).

Substantially flat bars 42 may be used in order to support the lead impregnated polymer of the shield 30 on the non-folding or non-bending parts or regions of the shield 30. The bars 42 may serve as horizontal spars to support the lead impregnated polymer of the shield 30 and to pull the shield 30 downward on opposite sides of a rod 40 in order to be folded in an orderly manner as the shield 30 is extended and retracted (as shown in FIG. 3). Furthermore, the flat bars 42 may provide additional support to the shield 30 and allow the shield 30 to fold more compactly. The bars 42 are wider and optionally flatter than the rods 40.

In order to both provide support to the shield 30 and potentiate the attenuation of the radiation 122, the rods 40 and the bars 42 may be made out of a suitable radiation-blocking, radiopaque material that also provides sufficient structural support, including but not limited to aluminum. Therefore, the rods 40 and the bars 42 may help the shield 30 further block radiation 122.

The rods 40 and the bars 42 may be bonded to the shield 30 in order to provide proper support and to fold the shield 30 properly. The rods 40 and the bars 42 may be bonded to the shield 30 with, for example, a resin, such as an epoxy resin. The epoxy resin may appropriately bond the aluminum rods 40 and the aluminum bars 42 to the lead impregnated polymer or polyurethane of the shield 30.

The rods 40 and the bars 42 may be spaced apart from each other along the length of the shield 30 in order to provide sufficient vertical support and symmetry in order to properly fold the shield 30 when the shield 30 is in the retracted position 32 or the partially extended position 34 and to allow the shield 30 to extend. According to one embodiment as shown in FIG. 4, the distance DR between each of the rods 40 along the length of the shield 30 (when the shield 30 is in the extended position 36) is approximately 2-10 inches, more preferably 4-8 inches, or most preferably 6 inches.

According to one embodiment as shown in FIG. 4, the distance DB between each of the bars 42 along the length of the shield 30 is approximately 0.5-5 inches, more preferably 2-4 inches, or most preferably 3 inches when the shield 30 is in the extended position 36. Accordingly, either side of the rods 40 may be approximately 1.5 inches from one of the bars 42.

The spacing of the rods 40 and the bars 42 relative to and along the length of the shield 30 may vary according to the desired configuration and amount of support. According to one embodiment as shown in FIG. 4, for example only, the distance B1 between the end of the first bar 42 and the opposite end of the shield 30 may be approximately 24 inches, the distance B2 between the end of the sixth bar 42 and the end of the shield 30 may be approximately 9 inches, the distance B3 between the end of the seventh bar 42 and the end of the shield 30 may be approximately 6 inches, the distance R1 between the last fourth rod 40 and the end of the shield 30 may be approximately 5 inches, and the distance B4 between the last eighth bar 42 and the end of the shield 30 may be approximately 3 inches.

The rods 40 and bars 42 each extend along the majority (or all of) the width of the shield 30. Accordingly, the length of the rods 40 and the bars 42 may be approximately the same as the width WS of the shield 30. According to various embodiments, the length of the rods 40 and the bars 42 may be approximately 10 to 30 inches, more preferably 15 to 25 inches, or most preferably 18 inches.

According to one embodiment, the rods 40 may have a diameter of approximately $1/8$ to $3/4$ inches and a thickness of approximately $1/25$ to $2/5$ inches. More preferably, the rods 40 may have a diameter of approximately $1/4$ to $1/2$ inches and a thickness of approximately $2/25$ to $6/25$ inches. Most preferably, the rods 40 may have a diameter of approximately $3/8$ inches and a thickness of approximately $4/25$ inches (0.16 inches).

According to one embodiment, the bars 42 may have a width of approximately 0.25 to 2 inches and a thickness of approximately $1/32$ to $1/2$ inches. More preferably, the bars 42 may have a width of approximately 0.5 to 1.5 inches and a thickness of approximately $1/16$ to $1/4$ inches. Most preferably, the bars 42 may have a width of approximately 1 inch and a thickness of approximately $1/8$ inches.

However, it is understood that various dimensions and relative positions of the rods 40 and/or the bars 42 may be larger or smaller.

The Rail Assembly

The rail frame or assembly 50 (as shown in FIGS. 5A-7) may provide support to the shield 30 and allow the shield 30 to be moved along a portion of the length of the table 110 (e.g., along the length of the rail assembly 50) in order to provide more or less shielding to the patient 10 and to change which areas of the patient's body (and the table 110) are exposed to radiation 122 for examination and which areas of the patient's body (and the table 110) are protected from radiation 122. Furthermore, the rail assembly 50 is configured to position the shield 30 in between the table 110 and the radiation source 120, in particular such that the shield 30 is positioned below the table 110 and above the radiation source 120.

The rail assembly 50 comprises at least one rail 51 that the shield 30 is movable along between the retracted position 32 and the extended position 36. As shown in FIG. 5A, the rail assembly 50 may be a dual rail system. Accordingly, the rail assembly 50 may include (optionally among other components, as described further herein) at least two runners, tracks, or rails 51 that extend along the length of the rail assembly 50 and are substantially parallel to each other. The rails 51 are positioned on opposite sides of the shield 30 (along the width of the shield 30) and support and guide the movement of the shield 30 along the table 110. The opposite sides of the shield 30 may optionally partially or fully overlap with each of the rails 51. Each side of the shield 30 (along the width of the shield 30) may be movably attached to one of two rails 51 (as described further herein) to allow the practitioner to pull or extend the shield 30 along the length of the rails 51.

Figure 6:
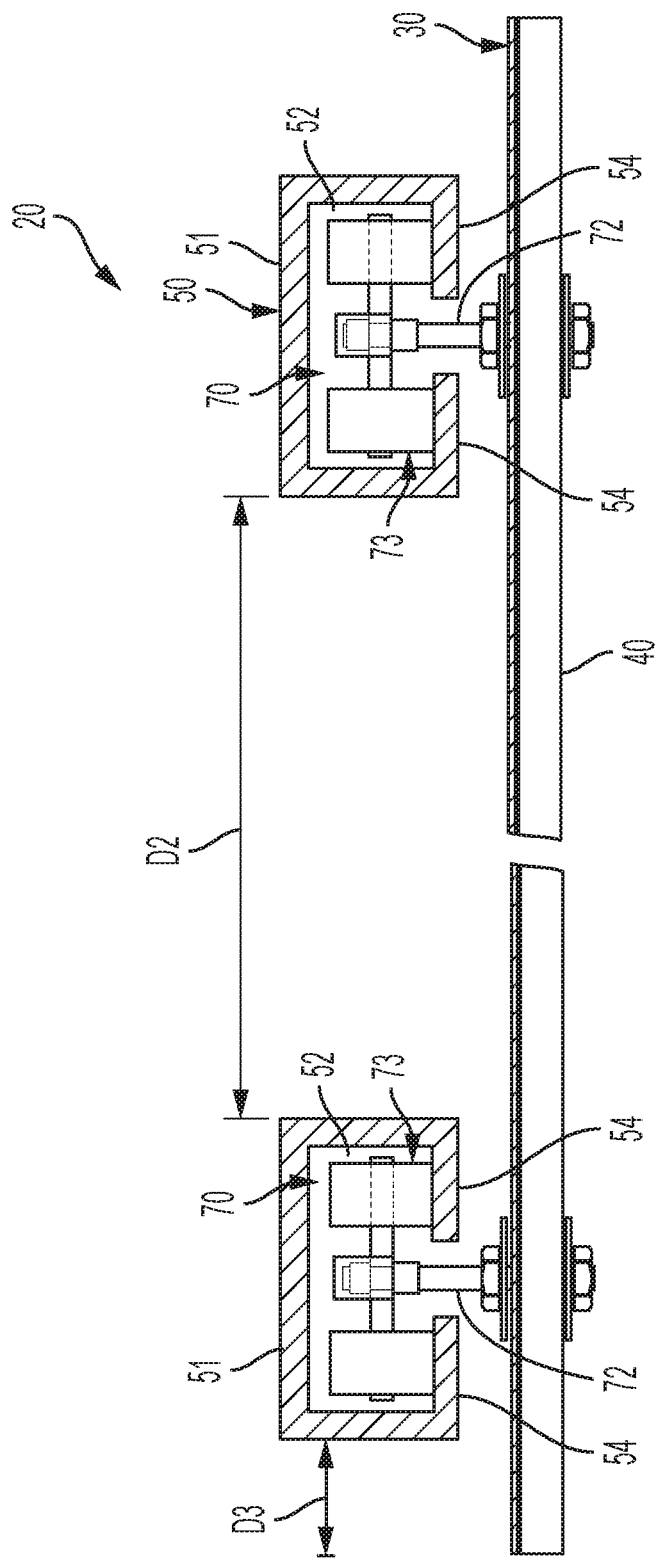
FIG. 6 is a cross-sectional, partially transparent view through the radiation shield assembly of FIG. 3.
Figure 7:
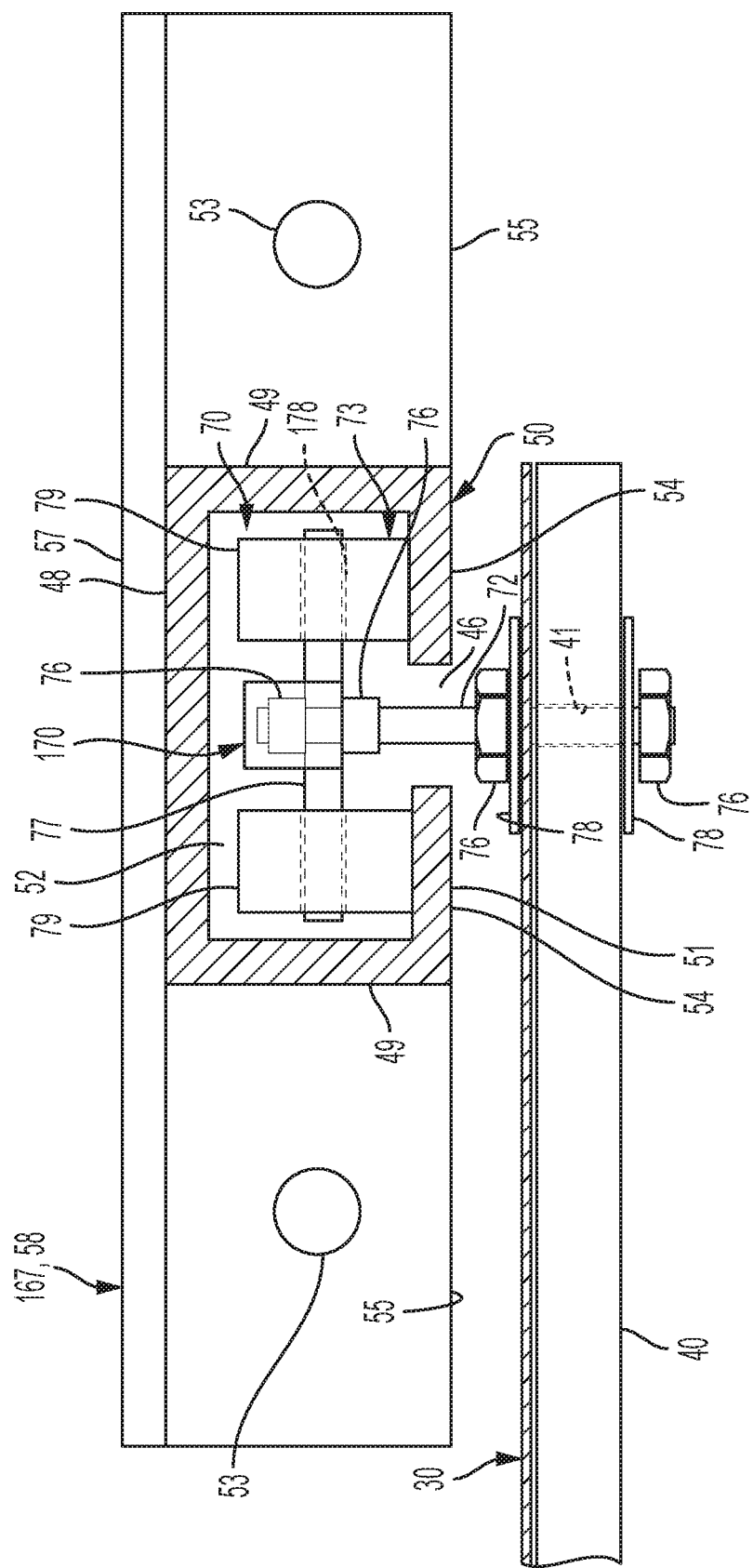
FIG. 7 is a cross-sectional, partially transparent view of portion of the radiation shield assembly of FIG. 3.

As shown in FIGS. 6-7, the rails 51 each include and define a slot 52. A portion of each of the shield adjusters 70 (as described further herein) is configured to move within and along the slot 52 as the shield 30 is moved. Accordingly, the slot 52 is large enough for a top portion of the shield adjuster 70 (such as the roller structure 73, as described further herein) to move along and within the slot 52 (which allows the shield 30 to be moved between the retracted position 32, the partially extended position 34, and the extended position 36).

As shown in FIGS. 6-7, the rails 51 each also include a top wall 48, two side walls 49, two lips 54, and a longitudinal opening 46, each of which define a portion of the slot 52 and extend along the length of the rail 51 (and therefore also along the length of the slot 52). The top wall 48 is substantially opposite the two lips 54 and the longitudinal opening 46 along the height of the rail 51, and the two side walls 49 are substantially opposite each other along the width of the rail 51. The longitudinal opening 46 leads into an inner area of the slot 52 within the rail 51 along the length of the rail 51 and through at least one longitudinal end 44 of the rail 51.

As shown in FIGS. 6-7, the two protruding edges or lips 54 are positioned on either side of the opening 46 to the slot 52 and extend longitudinally along the length of either side of the longitudinal opening 46 and along the length of the rail 51. The two lips 54 together only extend along a portion of the width of the rail 51 in order to define the longitudinal opening 46 therebetween. The width of the opening 46 defined by the lips 54 is less than the width of a top portion of the shield adjuster 70 (and more wide than a middle portion of the shield adjuster 70), and the width within the slot 52 is larger than the width of the top portion of the shield adjuster 70 such that the top portion of the shield adjuster 70 is secured within and movable along the slot 52 (without falling through the opening 46) to allow the position of the shield 30 to be adjusted relative to the rail 51.

The rail 51 (including the slot 52) extends lengthwise in a longitudinal direction between two longitudinal ends 44 as shown in FIG. 5A. At least during assembly, the rails 51 may be substantially open along one or both of their longitudinal ends 44 in order to provide an area to insert the top portion of the shield adjuster 70 into the slot 52 of the rail 51 during assembly. Once assembled, in order to prevent the shield adjuster 70 from falling out of the slot 52 (and thereby detaching the shield 30 from the rail assembly 50), the rail assembly 50 may include a locking pin or stopper 43 and a pair of corresponding holes near one or both of the longitudinal ends 44. The stopper 43 is longer than the width of the rail 51, which prevents the stopper 43 from falling out of the pairs of holes. Furthermore, the stopper 43 may include a head and a shaft. The shaft fits within and extends through the pair of holes, while the head (which is larger than the holes) prevents the stopper 43 from moving completely through the pair of holes. The holes may extend through opposite sides of the rail 52 (such as through each of the side walls 49). Accordingly, at each of the longitudinal ends 44, the shaft of the stopper 43 is inserted through the pair of corresponding holes, which prevents any of the shield adjusters 70 from falling out of the slot 52. The stopper 43 may optionally include a spring-activated detent in order to keep the stopper 43 in the holes during use and allow the stopper 43 to be removed by the user when needed (e.g., when the shield 30 needs to be removed).

The size of the rails 51 may vary according to the desired configuration. According to one embodiment, the rails 51 may have an outer width (i.e., the distance between the respective opposite outer surfaces of the two side walls 49) of approximately 0.25-1.5 inches and a height (i.e., the distance between the respective opposite outer surfaces of the top wall 48 and the lips 54) of approximately 0.25-1.5 inches. More preferably, the rails 51 may have an outer width of approximately 0.5-1 inches and a height of approximately 0.5-1 inches. Most preferably, the rails 51 may have an outer width of approximately 0.75-0.90 inches and a height of approximately 0.50-0.75 inches. According to one embodiment, the inner width of the slot 52 of the rail 51 (i.e., the distance between the respective opposite inner surfaces of the side walls 49) may be approximately 0.73 inches and the thickness of each of the walls of the rail 51 (in particular the lips 54) may be approximately 0.085 inches. The total width of one of the lips 54 (i.e., the distance between the respective opposite outer surfaces of one of the side walls 49 and a respective one of the lips 54) may be approximately 0.33 inches and the distance from an inner surface of a side wall 49 of the rail 51 to the end of the lip 54 may be approximately 0.245 inches.

As shown in FIGS. 5A-5B and 12-13A, the rail assembly 50 may further include a variety of other different components, including but not limited to, at least one cross-beam 56, at least one mount support 167 (e.g., one-sided extensions 58 and/or two-sided extensions 168), and/or at least one corner support 59. Accordingly, the rail assembly 50 may have a variety of different configurations. For example, the rail assembly 50 may only include the rails 51 or may include additional components. Furthermore, the rail assembly 50 may include or be attachable to a portion of the table mounts 157 (as described further herein).

As shown in FIG. 5A, the rail assembly 50 may include at least one runner, brace, or cross-beam 56 that is substantially perpendicular to and attaches to each of the rails 51. The cross-beam 56 provides additional support and stability to the rail assembly 50 and maintains the relative position of the rails 51 to each other along the width of the rail assembly 50. At least one cross-beam 56 may be positioned on one of the ends of each of the rails 51. Alternatively or additionally, another cross-beam 56 may optionally be positioned in a middle portion of the rails 51 along the length of the rail assembly 50. One end of the rail assembly 50 may be substantially open (i.e., without a cross-beam 56) in order to provide an area to attach the shield 30 to the rail assembly 50.

As further shown in FIG. 5A, the rail assembly 50 may include at least one corner support 59 that is attached to and extends along each of the cross-beam 56 and the rail 51 (at the intersection or joint of the cross-beam 56 and the rail 51) in order to stabilize and increase the structural integrity of the cross-beam 56 and the rail 51 and to keep tension within the rail assembly 50. The corner support 59 may be, for example, a flat sheet of support material that is approximately triangular. The corner support 59 may extend along a length of approximately 4.50 inches of each of the cross-beam 56 and the rail 51. The corner support 59 may optionally be adhered (with, for example, epoxy) to a cross-beam 56 and a rail 51.

Figure 12:
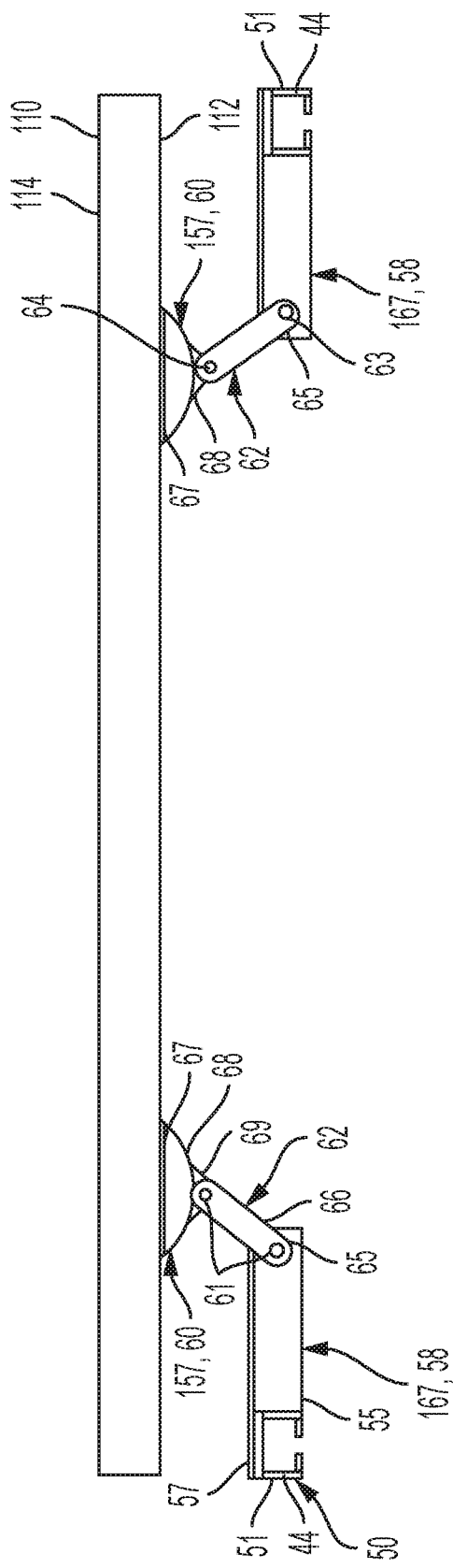
FIG. 12 is a side view of a suction mount of a radiation shield assembly according to one embodiment attaching a rail assembly to a table.
Figure 13A:
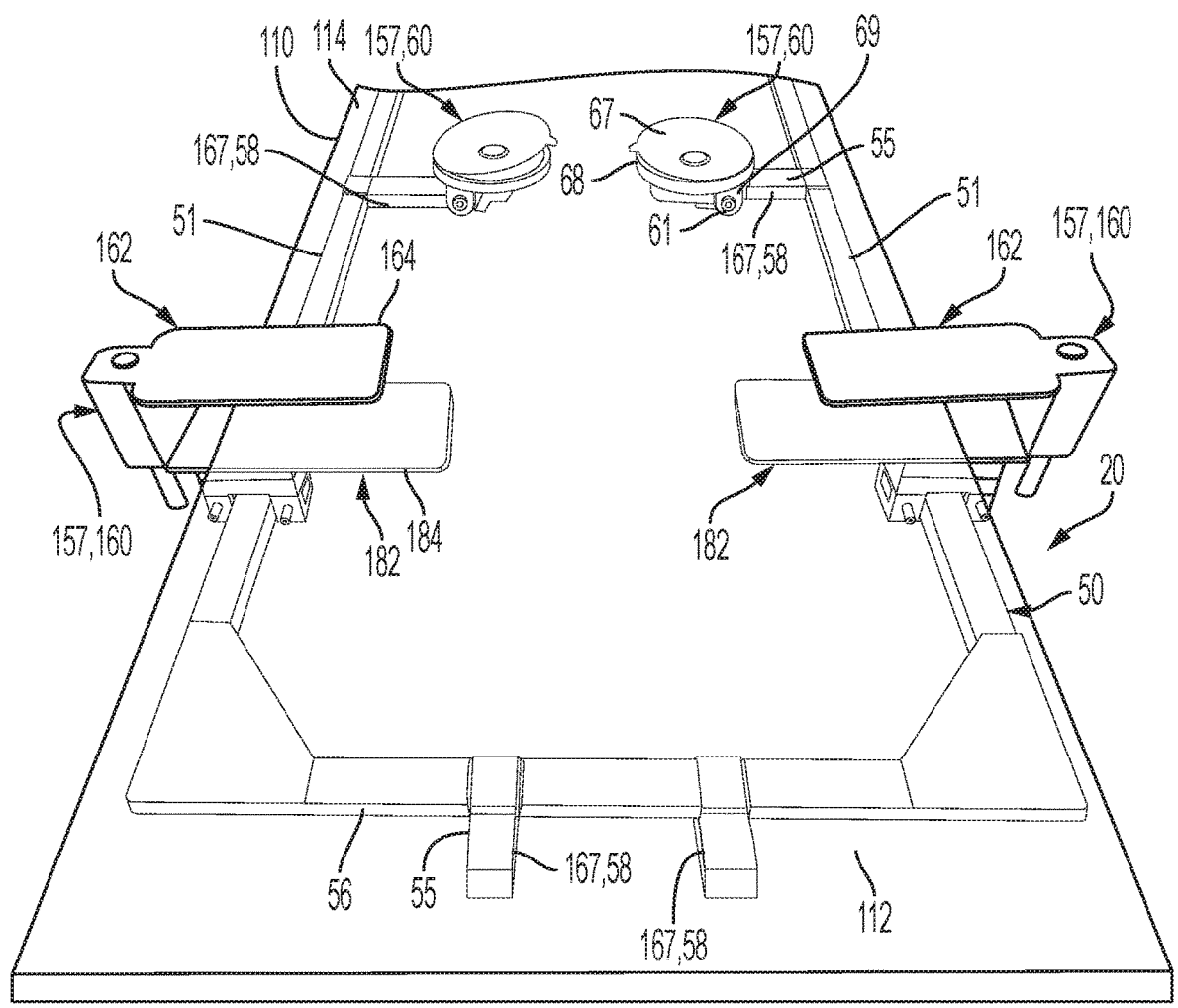
FIG. 13A is a perspective, partially transparent view of a radiation shield assembly with clamp mounts and suction mounts attached to a table according to one embodiment.

Even further, the rail assembly 50 may include at least one bracket or mount support 167 that is positioned along and extends substantially perpendicularly from one of the rails 51 or the cross-beams 56. The mount support 167 is configured to support and attach to the table mounts 157 directly or indirectly (as described further herein) to attach the rail assembly 50 (and the shield 30) to the table 110. The mount support 167 may be a one-sided extension 58 (as shown in FIGS. 12 and 13A) or a two-sided extension 168 (as shown in FIG. 5A), as described further herein. The rail assembly 50 may optionally include a combination of different mount supports 167 that are one-sided extensions 58 and/or two-sided extensions 168 and are positioned along the rails 51 and/or the cross-beams 56.

As shown in FIG. 5A, two mount supports 167 are positioned on and statically attached to each of the rails 51. The mount supports 167 may be positioned in a variety of different locations along the rails 51. According to one embodiment, a first mount support 167 may be positioned along the rail 51 at a distance of approximately 4-5 inches from the end of the rail assembly 50 (and the longitudinal end 44 of the rail 51), and a second mount support 167 may be positioned along the rail at a distance of approximately 19.75-21.50 inches from the end of the rail assembly 50 (and the longitudinal end 44 of the rail 51).

Additional mount supports 167 may also be positioned in a variety of different locations along the cross-beams 56. For example, a first mount support 167 may be positioned along the cross-beam 56 at a distance of approximately 6 inches from a side of the rail assembly 50 and a second mount support 167 may be positioned along the cross-beam 56 at a distance of approximately 10 inches from the side of the rail assembly 50.

Figure 5B:
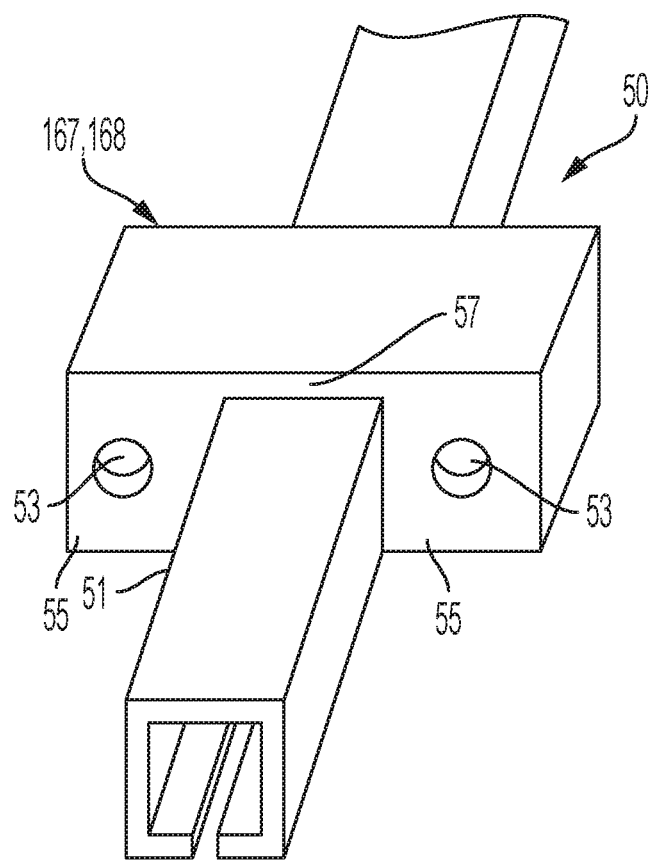
FIG. 5B is a perspective view of a portion of the rail assembly of FIG. 5A.

The shape of the mount supports 167 may vary according to the desired configuration (and according to whether the mount support 167 is a one-sided extension 58 or a two-sided extension 168, as described further herein). Although the rail 51 is referred to herein, it is understood that the mount supports 167 may be attached to the cross-beams 56 in a similar manner. As shown in FIGS. 5B and 7, the mount support 167 includes an overlapping portion 57 and at least one base 55.

The overlapping region or portion 57 of the mount support 167 extends beyond the end of the base 55 and may be an extension of a top wall of the base 55. The overlapping portion 57 is configured to extend over and overlap both the base 55 and the top wall 48 of the rail 51 once assembled to the rail 51 in other to further secure and attach the mount support 167 to the rail 51. Accordingly, the length of the overlapping portion 57 (i.e., the amount that the overlapping portion 57 extends beyond the base 55) may be approximately equal to (or less than) the width of the rail 51, as shown in FIG. 7.

The base 55 of the mount support 167 provides an area for the table mount 157 to attach to the entire mount support 167 (and thus to the rail assembly 50). As shown in FIG. 7, when the mount support 167 is assembled to the rail 51, an end of the base 55 (that which the overlapping portion 57 extends from) is positioned next to and abuts one of the side walls 49 of the rail 51 such that the base 55 extends along the height of the rail 51.

If the mount support 167 is a one-sided extension 58 (according to one embodiment as shown in FIG. 12), the mount support 167 includes only one base 55 that is positioned on one side of the overlapping portion 57. The overlapping portion 57 extends beyond the end of the base 55 of the one-sided extension 58 as a lip that overlaps the top wall 48 of the rail 51. Accordingly, the base 55 (and therefore the one-sided extension 58) extends out from and along only one side of the rail 51 (i.e., an inner or outer side wall 49), and the one-sided extension 58 does not straddle the rail 51. The one base 55 can be positioned on either side of the rails 51 and thereby can extend inwardly or outwardly from each of the rails 51 (or the cross-beam 56) depending on the configuration. For example, as shown in FIG. 13A, the bases 55 of some of the one-sided extensions 58 (i.e., the mount supports 167) extend inwardly from the rails 51, while other bases 55 of some of the one-sided extensions 58 extend outwardly from the cross-beam 56 at the end of the rails 51. As described further herein, the one-sided extension 58 is particularly useful for attaching the suction mount 60 to the rail assembly 50.

The bases 55 of the mount supports 167 may have a shorter or longer length, depending on the desired configuration. In particular, the length of the one-sided extension 58 may depend on the width of the table 110 that the radiation shield assembly 20 is to be attached to and used with. For example, a one-sided extension 58 with a greater length may accommodate and fit with a larger variety of tables 110 with different widths. According to one embodiment, the length of the one-sided extension 58 (including both the base 55 and the overlapping portion 57) may be approximately 3.0 to 3.65 inches, and the length of the base 55 may be approximately 2.0 to 2.75 inches (as shown in FIG. 7). However, the shorter one-sided extension 58 may mount the rail assembly 50 to the table 110 more securely. For example, according to another embodiment, the length of the one-sided extension 58 (including both the base 55 and the overlapping portion 57) may be approximately 1.60 to 1.625 inches, and the length of the base 55 may be approximately 0.750 inches.

If the mount support 167 is a two-sided extension 168 (according to another embodiment as shown in FIGS. 5A-5B and 7), the mount support includes two bases 55 that are positioned on opposite sides of the overlapping portion 57. The overlapping portion 57 extends between ends of the two bases 55 of the two-sided extension 168 as a bridge connecting the two bases 55 and overlaps the top wall 48 of the rail 51. The two-sided extension 168 thus straddles the rail 51, which helps equalize the pull on either side of the rail 51 to prevent torque from being applied to the rail 51. Accordingly, two bases 55 (and therefore the two-sided extension 168) extend from and along opposite sides of the rail 51 (i.e., both side walls 49) (with the overlapping portion 57 positioned between the bases 55 and on top of the rail 51). Thus, the two-sided extension 168 extends both inwardly and outwardly from two opposite side walls 49 of the rail 51. As described further herein, the two-sided extension 168 is particularly useful for attaching the clamp mount 160 to the rail assembly 50. As a two-sided extension 168, the length LL of the mount support 167 (including both of the bases 55 and the overlapping portion 57) may be approximately 2.30 inches, and the length LB of one of the bases 55 may be approximately 0.650 inches (as shown in FIG. 5A), according to one embodiment as shown in FIG. 5A.

As shown in FIG. 5B, the base 55 includes an aperture or hole 53 that extends completely through the base 55 and provides an area for a portion of the table mount 157 to attach to the mount support 167. In order to attach the mount support 167 and the table mount 157, a fastener (e.g., a screw, pin, or bolt 61) may extend both through the hole 53 of the mount support 167 and through at least one corresponding hole in the table mount 157. If the mount support 167 is the one-sided extension 58, the table mount 157 attaches just to the one base 55. If the mount support 167 is the two-sided extension 168, the table mount 157 attaches to both of the two bases 55.

The hole 53 may be configured in a variety of different manners. According to one embodiment, each of the bases 55 includes two separate apertures that define the hole 53. The two apertures extend completely through two opposite walls, are aligned with each other, and are substantially the same size such that the bolt 61 can be positioned within and extend through both of the apertures.

According to another embodiment, the base 55 may include a tube that extends within an inner center space or area of the base 55. The tube may extend between and connect the two apertures in each of the two opposite walls of the base 55 and extend along the entire length of the hole 53 through an inner center area of the base 55, thereby defining at least a center portion of the hole 53 along its length. The inner diameter of the tube (or the hole 53) may be approximately 0.170 to 0.175 inches and the outer diameter of the tube may be approximately 0.25 inches.

The inner center area of the base 55 may optionally be filled with a filling around the hole 53 (and any tube the hole 53 may include), such as an adhesive (i.e., as epoxy and resin), for additional strength and to create a substantially solid core within the base 55 (aside from the hole 53 and any tube the hole 53 may include). With the inner center area of the base 55 filled with the filling, the base 55 may or may not include the tube. For example, without the tube, the filling within the base 55 may define at least a portion of length of the hole 53 within the inner center area of the base 55.

In order to attach the mount support 167 to the rail 51, various portions (such as the underside of the overlapping portion 57 and an inner wall of the base 55) of the mount support 167 may be covered in an adhesive (such as epoxy or resin), and then placed onto (and thereby adhered to) the rail 51. Although the rail 51 is referenced herein, it is understood that the mount supports 167 may be attached to the cross-beam 56 in a similar manner.

The size of the mount support 167 may vary according to the desired configuration. According to various embodiments, the thickness of the overlapping portion 57 may be approximately 0.150 inches. The width of the entire mount support 167 (including both the base 55 and the overlapping portion 57) may be constant along the length of the mount support 167. According to one embodiment, the width of the mount support 167 may be approximately 0.90 inches and the height of the mount support 167 may be approximately 0.50 inches. The distance between inner surfaces of the sides walls of the mount support 167 (i.e., the width of the inner region of the base 55) may be approximately 0.73 inches.

The rail assembly 50 (and various components of the rail assembly 50) may have a variety of different dimensions according to the desired configuration. The length of the rail assembly 50 (and, specifically, the length of the rails 51) may be slightly longer than the length LS (as shown in FIG. 4) of the shield 30 in order to allow the shield 30 to completely expand into the extended position 36 (if desired by the practitioner) and to securely support the shield 30. For example, if the length LS of the shield 30 is approximately 30 inches, the length of the rail assembly 50 (including both the length of the rails 51 and the width of the cross-beam 56) may be approximately 31-34 inches (i.e., 32 inches) and the length of the rails 51 may be approximately 30.10 to 31 inches. According to another embodiment, the length of the rail assembly 50 is approximately 27 inches, and the length of the rails 51 is approximately 26.10 inches (and the length LS of the shield 30 may be sized accordingly).

The two rails 51 may be spaced apart from each other according to the width WS of the shield 30 and the corresponding length of the rods 40 and the bars 42. Accordingly, the length of the cross-beam 56 (i.e., the width of the entire rail assembly 50), which may determine the distance between the two rails 51, may be approximately equal to the width WS of the shield 30. For example, if the width WS of the shield 30 is approximately 16.50 to 18 inches, the rails 51 may be approximately 16.50 to 18 inches apart from each other and the length of the cross-beam 56 may be approximately 16.50 to 18 inches long. Alternatively, the shield 30 may optionally be wider than the distance between the rails 51 and the length of the cross-beam 56. For example, as shown in FIG. 6, the shield 30 may extend a distance D3 beyond the outer edges of each of the rails 51. The distance D3 may be approximately 0.750 inches.

The distance between an inner edge of one rail 51 to an outer edge of the other rail 51 may be approximately 15.60 inches. As shown in FIG. 6, the distance D2 between the inner edges of the two rails 51 may be approximately 15 inches. The distance between the rails 51 and the length of the cross-beam 56 may also depend on the size (e.g., the width) of the table 110.

In order to prevent any interference of the rail assembly 50 with the radiation 122 that is intended to enter the patient 10 for examination purposes and to prevent any interference that may affect the imaging of the patient's body, the rail assembly 50 may be constructed out of a material (or materials) that does not block or otherwise materially affect radiation 122 and is radiotranslucent (such that x-rays pass through the rail assembly 50), radiotransparent, or radiolucent. Radiotranslucent, radiotransparent, and radiolucent materials are each permeable to radiation and do not block radiation. Instead, radiotranslucent materials allow radiation to pass through the material and therefore do not affect the imaged area of the patient's body, even if it is in the field of view. For example, the rail assembly 50 may be constructed out of carbon fiber, which is radiotranslucent. Different types, thicknesses, and weaves of carbon fiber may be used depending on the desired configuration in order to increase the strength of the rail assembly 50 and prevent the rail assembly 50 from ripping or breaking. For example, various portions of the rail assembly 50 may include, for example, several plys of unidirectional carbon fiber with a two ply or layer exterior or may have a 3 k plain weave along the long axis. The various layers of carbon fiber may have offset patterns to increase the strength of the rail assembly 50. The top, sides, and bottom of the rail assembly 50 may have the same or different thicknesses or number of layers of carbon fiber. Furthermore, portions of the rail assembly 50 may optionally be infused with resin. Accordingly, the rail assembly 50 will not obstruct the practitioner's field of view while the radiation shield assembly 20 in place and will allow the practitioner to still completely visualize the patient without the rail assembly 50 blocking or impeding any of the view (in particular while the shield 30 is in the retracted position 32 or the partially extended position 34), even if a portion of the rail assembly 50 is within the field of view and the direct radiation beam 121 of the radiation 122.

Additionally, the rails 51 may optionally be tested for binding by identifying and removing any obstructions, burrs, or narrowing along the inside or interior of the rail 51

(i.e., within the slot 52) that may prevent or impede the movement of the roller structure 73 and/or the handle 140 along the rail 51.

Shield Adjuster

As shown in FIGS. 6-7, the shield 30 may be movably or slidably mounted and attached to each of the two rails 51 through a plurality of shield adjusters 70. The shield adjusters 70 are attached to the shield 30 and configured to allow the shield 30 to move (e.g., roll) along the length of the rail assembly 50. As shown in FIG. 6, two shield adjusters 70 (corresponding to the two rails 51) may be positioned on and attached to opposite sides of the shield 30 (along the width of the shield 30). In particular, the shield adjusters 70 are attached to each rod 40 and movably attached to respective rails 51 such that movement of the shield 30 causes the shield adjusters 70 to move along the rails 51. In particular, a top potion (i.e., the roller structure 73 and a top portion of the bolt 72) of each of the shield adjusters 70 is configured to move within and along the slot 52 of the rail 51. As shown in FIGS. 3-4, multiple shield adjusters 70 may be attached to the shield 30 along the length of the shield 30 in order to support the shield 30 along the length of the shield 30.

Figure 8:
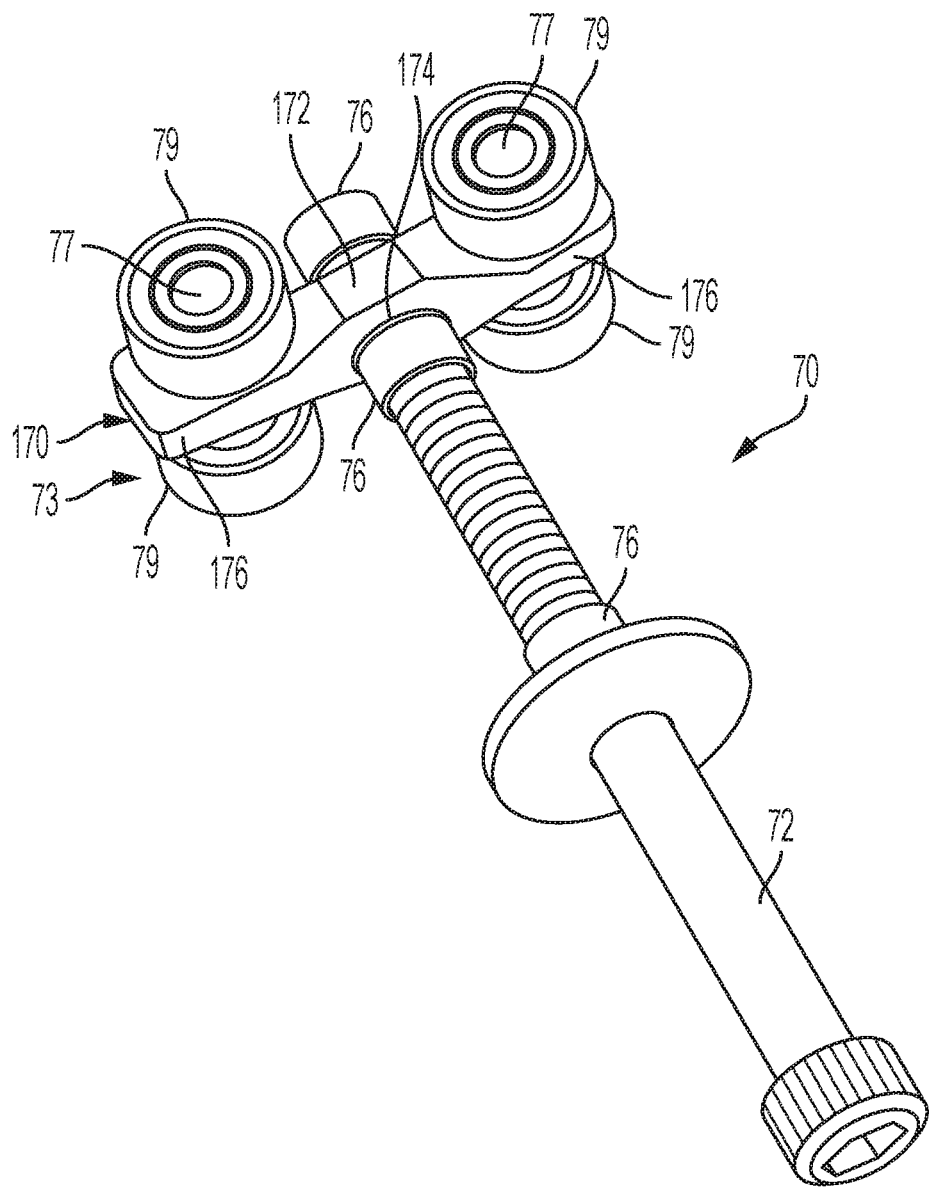
FIG. 8 is a perspective view of a shield adjuster of the radiation shield assembly of FIG. 3.
Figure 9:
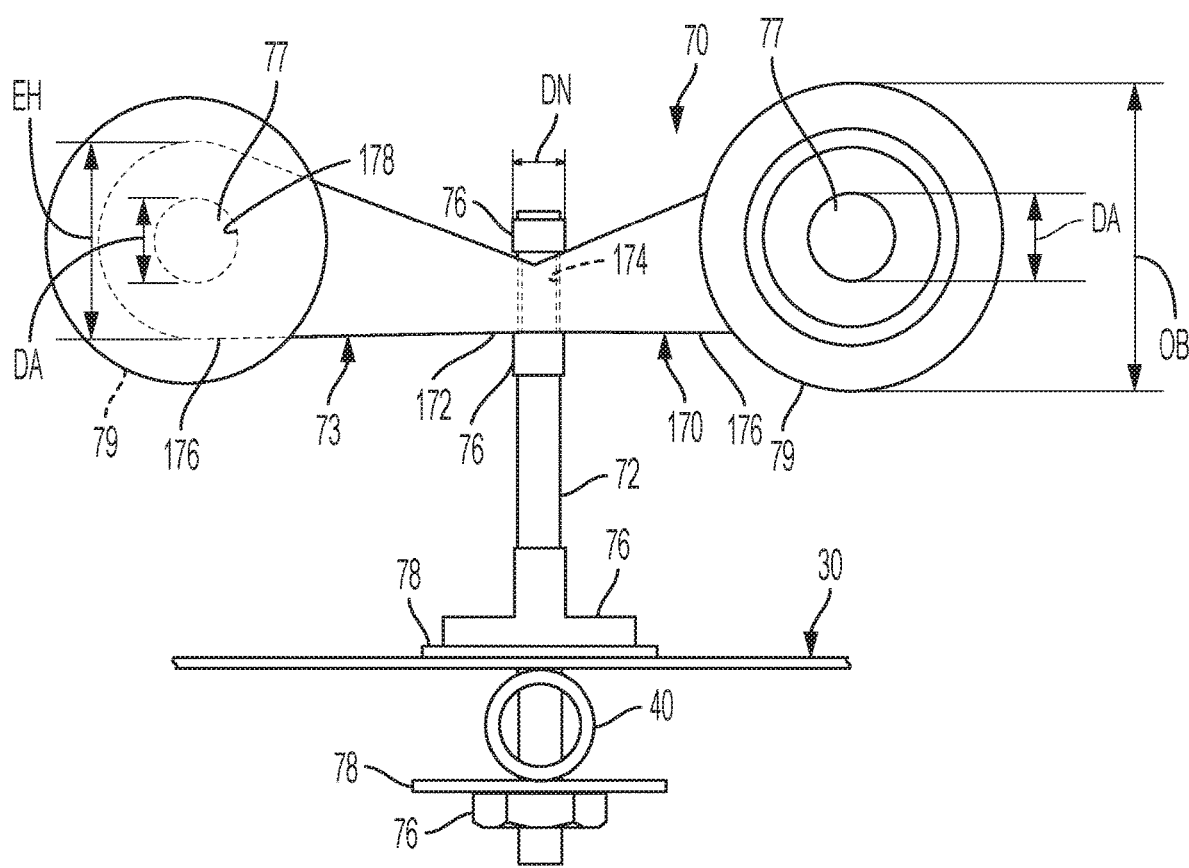
FIG. 9 is a side, partially transparent view of the shield adjuster of FIG. 8 attached to a shield and a rod.

As shown in FIGS. 8-9, the shield adjuster 70 includes a fastener (e.g., a screw, pin, or bolt 72) and a roller structure 73. The bolt 72 attaches to and extends upward from the rod 40 and the shield 30 (as shown in FIGS. 6-7 and 9 (as well as FIG. 4)). The bolt 72 attaches a portion of the shield 30, the rod 40, and a roller structure 73 together such that movement of one of the shield 30 (and the rod 40) or the roller structure 73 causes the other of the shield 30 (and the rod 40) and the roller structure 73 to move relative to the rail 51. The roller structure 73 movably attaches to one of the rails 51 such that the shield 30 can be moved along the length of the rails 51. The bolt 72 and the roller structure 73 are attachable to each other such that the bolt 72 (and thus the shield 30 and the rod 40) moves congruently with the roller structure 73 as the roller structure 73 moves or rolls along the rail 51.

As shown in FIGS. 6-7 and 9, the bolt 72 of the shield adjuster 70 extends substantially perpendicularly through both the shield 30 and one of the rods 40. The bolt 72 may extend through the rod 40 (in addition to the shield 30) in order to more fully support the shield 30 and securely attach the shield 30 to the rails 51 (in particular since, for example, the shield 30 may be flexible and the rod 40 may be more rigid). The bolt 72 of the shield adjuster 70 may be, for example only, a 10-24×1¼ inch pan Phillips machine screw or an 8 millimeter bolt. The bolt 72 may be smooth and/or threaded along its length.

Accordingly, each rod 40 may include a hole 41 (as shown in FIG. 7) on either end that the bolt 72 may extend through. The bolt 72 may further extend through a corresponding hole in the shield 30 (that aligns with the hole 41 of the rod 40), through the longitudinal opening 46 of the rail 51, into the slot 52 of the rail 51, and through a center hole 174 in the roller structure 73 (as shown in FIG. 9) in order to movably attach the rod 40 and the shield 30 to the rail 51. According to one embodiment, the hole 41 in the rod 40 may be a drilled hole, and the diameter of the hole 41 may be approximately 3/16 inches. Each of the holes 41 may be positioned approximately 2 inches from each end of the rod 40 and the bolt 72 may extend through the hole 41 in the rod 40 (and may optionally further be adhered (with, for example, epoxy) to the rod 40 for additional structure and strength).

As shown in FIGS. 7 and 9, various mounting hardware, such as bushings or nuts 76, may be positioned along the length of the bolt 72 on either side of the rod 40 and the shield 30 to secure the rod 40 and the shield 30 along the length of the bolt 72. The nuts 76 may be, for example only, a 10-24 hex nuts. The nuts 76 may each be the same type of nut or different types of nuts, depending on the desired configuration.

In order to protect and buffer the rod 40 and the shield 30 from the nuts 76, a protective washer 78 may be positioned between each of the nuts 76 and the rod 40 and the shield 30. The protective washers 78 may be, for example only, a ½×1/16 inch rubber washers.

The roller structure 73 of the shield adjuster 70 allows the shield adjuster 70 to movably attach to the rail 51 and is configured to move along or roll within the slot 52 of the rail 51. As shown in FIGS. 6-7 and 9, the roller structure 73 is positioned along the top portion of the shield adjuster 70 such that at least the majority of the bolt 72 (in particular the bottom portion of the bolt 72 that attaches to the shield 30 and the rod 40) is below the roller structure 73, and thus the shield 30 and the rod 40 hang below the roller structure 73 (and the rail 51) when the shield adjuster 70 is attached to the rail assembly 50. Accordingly, at least the majority of the roller structure 73 (e.g., the base 170, the axles 77, and/or the wheels 79) may be positioned within the slot 52 when assembled to the rail assembly 50.

As shown in FIGS. 7-9, the roller structure 73 includes a base 170, at least one horizontal axle 77, and at least two wheels 79 (i.e., at least one pair of wheels 79). According to one embodiment, the roller structure 73 includes two horizontal axles 77 and four wheels 79 (i.e., two pairs of the wheels 79 that are each positioned along a respective horizontal axle 77, as described further herein). This configuration of the roller structure 73 (i.e., having two horizontal axles 77 and four wheels 79) increases the stability of the roller structure 73 and allows the roller structure 73 (and therefore the shield 30) to easily move along the length of the rail 51 (within the slot 52) without binding, even if the user exerts force onto portions of the radiation shield assembly 20 in directions that do not extend along the direction of the length of the rail 51 along which the shield 30 is configured to move (i.e., forces in the vertical direction and/or in the width direction of the rail 51).

The body, carriage, or base 170 is attached to and positioned along a top portion of the bolt 72 (that is within the slot 52 when assembled) and attaches the wheels 79 to the bolt 72 (via the horizontal axles 77). Accordingly, as shown in FIGS. 8-9, the base 170 includes a center portion 172 with a center hole 174 that is surrounded on opposite ends (along the lengthwise direction of the base 170, which corresponds to the lengthwise direction of the rail 51 when assembled and the direction of movement of the shield 30) by two end portions 176, each of which end portions 176 include an end hole 178. The center portion 172 (and its corresponding center hole 174) and the end portions 176 (and their corresponding the end holes 178) are all sufficiently spaced apart from each other along the lengthwise direction of the base 170 such that, when assembled, the outer edges of the center portion 172 do not interfere with or hit either of the wheels 79 that are positioned along the end portions 176. According to one embodiment, the total length of the base 170 is approximately 1 inch, and the distance between the centers of each of the end holes 178 is approximately 0.645 inches. Each of the center hole 174 and the end holes 178 extend completely through the base 170.

As shown in FIGS. 8-9, the center hole 174 of the center portion 172 provides an area to receive and secure a top portion of the bolt 72 within the base 170, and the end holes 178 of the end portions 176 each provide an area to receive and secure a portion (e.g., a middle portion) of each of the horizontal axles 77. The longitudinal axis of the center hole 174 extends in a substantially perpendicular direction to the respective longitudinal axes of the end holes 178. Accordingly, when assembled, the horizontal axles 77 (that are within the end holes 178) are substantially perpendicular to the bolt 72 (that is within the center hole 174) due to the differences in orientations of each of the center hole 174 and the end holes 178.

As shown in FIGS. 8-9, the upper portion of the bolt 72 extends completely through the base 170 (through the center hole 174) such that the bolt 72 extends at least partially beyond both the top and bottom of the base 170. In order to prevent any binding while the radiation shield assembly 20 is being used, the center hole 174 of the base 170 does not have any internal threads and the inner diameter of the center hole 174 is slightly larger than the outer diameter of the bolt 72, which provides free play for the bolt 72 within the center hole 174 once assembled. Accordingly, the bolt 72 can free float, wiggle, swivel, and/or rotate within the center hole 174 once assembled and as needed, which prevents any torque from being applied to the roller structure 73, in particular if the user does not adjust the shield 30 in exactly the horizontal direction (i.e., along the length of the rails 51). According to one embodiment, the inner diameter of the center hole 174 may be sufficiently larger than the outer dimeter of the bolt 72 such that the bolt 72 is given ±15° of movement (i.e., a 30° arc) before applying torque to the base 170 (and therefore the roller structure 73).

As shown in FIGS. 8-9, the lengthwise direction of the base 170 (which corresponds to the length of the rail 51) extends in a substantially perpendicular manner to the bolt 72 (and substantially perpendicular to the horizontal axles 77). In order to secure the bolt 72 and the base 170 together, additional various mounting hardware, such as bushings or nuts 76, may be positioned along the length of the bolt 72 (i.e., above and below the base 170 along the length of the bolt 72), thus sandwiching and securing a portion of the base 170 between the nuts 76. The nuts 76 may be, for example only, threaded bushings.

According to one embodiment, the outer diameter DN of the uppermost nut 76 (i.e., the nut 76 above the base 170, as shown in FIG. 9) may be approximately 0.200 to 0.260 inches, which is larger than the inner diameter of the center hole 174 such that the top of the bolt 72 cannot move through the center hole 174 with the top nut 76 attached. Additionally, the outer diameter of the bolt 72 may be approximately 0.115 inches (where the respective inner diameters of the center hole 174 and the top nut 76 are slightly larger than outer diameter of the bolt 72 such that the bolt 72 fits within the center hole 174 and the top nut 76).

In order to allow sufficient room to secure a nut 76 along the top portion of the bolt 72 (above the base 170) while still providing enough clearance within the slot 52 (specifically along the height of the slot 52), the center portion 172 of the base 170 (that the bolt 72 extends through) has a smaller height than the end portions 176 of the base 170 (as shown in FIG. 9). This configuration provides additional room above the base 170 for both the top portion of the bolt 72 and the top nut 76 to fit within the height of the slot 52 above the base 170 (i.e., between the top of the base 170 and the bottom surface of the top wall 48 of the slot 52, as shown in FIG. 7). The end portions 176 of the base 170 have a greater height than the center portion 172 in order to allow the end holes 178 to be sufficiently large to receive the respective axle 77. For example, the height EH of the end portions 176 (and thus the maximum height of the base 170) may be approximately 0.240 inches (as shown in FIG. 9). However, the height of the end portions 176 of the base 170 are also smaller than the diameter of the wheels 79 in order to prevent any drag within the slot 52.

Each of the axles 77 extends completely through the base 170 (through a respective of one of the end holes 178) such that each of the axles 77 extends at least partially beyond both sides of the base 170. Accordingly, the wheels 79 may be attached to opposite ends of each of the axles 77 such that two wheels 79 are positioned along opposite sides of the base 170 along each axle 77 (as well as along both ends of the base 170 on opposite sides of the center hole 174). As shown in FIG. 8, the axles 77, the base 170, and the bolt 72 each extend, along their respective lengths, substantially perpendicularly to each other.

As shown in FIGS. 7-8, the rollers, ball bearings, or wheels 79 are each positioned toward an end of each of the axles 77 on opposite sides of the base 170 and allow the shield adjuster 70 to move freely along the length of the rail 51. Each of the wheels 79 is configured to roll along each of the top surfaces of the lips 54 within the slot 52 (as shown in FIG. 7) in order to move the shield adjuster 70 (and therefore, also the rod 40 and the shield 30) along the rail 51.

In order to allow sufficient room to position wheels 79 on opposite sides of the end portions 176 of the base 170 while still providing enough clearance within the slot 52 (specifically along the width of the slot 52), the end portions 176 of the base 170 (that the axles 77 for the wheels 79 extend through) have a smaller width than the center portion 172 of the base 170 (as shown in FIG. 8). This configuration provides additional room (e.g., "wheel wells") on both sides of the base 170 for both of the wheels 79 (as well as one of the end portions 176) to fit within the width of the slot 52 (i.e., between the inner surfaces of the two side walls 49 of the slot 52, as shown in FIG. 7). The center portion 172 of the base 170 has a greater width than the end portions 176 in order to allow the center hole 174 to be sufficiently large to receive the bolt 72. However, the center portion 172 of the base 170 is not too wide so as to avoid any interference with the inner edges of the wheels 79 once assembled.

The outer diameter OB of the wheels 79 may be less than the inner height of the slot 52 (as shown in FIG. 7) in order to provide sufficient room within the slot 52 for the roller structure 73 to move along the length of the rail 51. According to one embodiment as shown in FIG. 9, the outer diameter OB of the wheels 79 may be approximately 0.315 inches. The width of the wheels 79 may be approximately 0.156 inches. The wheels 79 may be constructed out of a variety of different materials, including but not limited to stainless steel or ceramic.

As shown in FIG. 9, the outer diameter DA of the axles 77 may be approximately 0.115 to 0.125 inches, where the respective inner diameters of the end holes 178 and the wheels 79 are slightly larger than the outer diameter DA of the axles 77 such that the axle 77 fits within the end holes 178 and the wheels 79.

The distance between the outer side edges of the wheels 79 along one axle 77 is larger than the width of the longitudinal opening 46 of the rail 51 in order to retain the roller structure 73 within the slot 52 (as shown in FIG. 7). According to one embodiment, the distance between the outer side edges of the wheels 79 along one axle 77 is approximately 0.560 inches, and the distance between the inner side edges of the wheels 79 along one axle 77 is approximately 0.250 inches.

Deflector

As shown in FIGS. 4 and 10, the radiation shield assembly 20 may include an angled support element or deflector 80 positioned on at least one longitudinal end of the shield 30. The deflector 80 is configured to both angle and support the angled end 39 of the shield 30 relative to the body 37 of the shield 30. The deflector and the angled end 39 of the shield 30 together further shield the patient 10 and the practitioners in a substantially vertical manner from radiation 122 (where the majority of the shield 30 (i.e., the body 37) shields in a substantially horizontal manner when unfolded in the extended position 36). In particular, the deflector 80 and the angled end 39 together help protect the patient 10 from scatter radiation 123 that may otherwise enter into the patient 10 through a vertical gap between the top surface of the body 37 of the shield 30 and the bottom surface 112 of the table 110.

The deflector 80 includes at least one support element. For example, as shown in FIG. 10, the deflector 80 includes two support elements (i.e., an upper brace or support element 82 and a lower brace or support element 86) that are positioned on opposite sides of and sandwich both a portion of the body 37 and a portion of the angled end 39 of the shield 30. The upper support element 82 may be positioned on the top of the shield 30 (i.e., between the shield 30 and the table 110), and the lower support element 86 may be positioned directly beneath the upper support element 82 on the bottom of the shield 30 (i.e., the other side of the shield 30).

The upper support element 82 and the lower support element 86 each include a horizontal portion 94 and a vertical portion 92 that are substantially perpendicular to each other such that the upper support element 82 and the lower support element 86 are each shaped in an "L." The horizontal portion 94 and a vertical portion 92 are angled at approximately 90° relative to each other in order to bend the body 37 and the angled end 39 of the shield 30 at approximately 90° relative to each other. Accordingly, the horizontal portion 94 extends along and parallel to the body 37 of the shield 30 (when the shield 30 is in the extended position 36), and the vertical portion 92 extends along and parallel to the angled end 39 of the shield 30.

Each of the upper support element 82 and the lower support element 86 may be continuous pieces of material. Since the shield 30 is sandwiched between and supported by the upper support element 82 and the lower support element 86, the upper support element 82 and the lower support element 86 bend the body 37 and the angled end 39 of the shield 30 relative to each other. The deflector 80 maintains the relative position of the body 37 and the angled end 39, regardless of the position and amount of folding of the shield 30. The upper support element 82, the shield 30, and the lower support element 86 may be attached together with bolts, in particular along the vertical portion 92 of the deflector 80 and the angled end 39 of the shield 30.

The upper portion of the angled end 39 of the shield 30 may optionally extend vertically above the vertical portion 92 of the deflector 80 in order to allow the upper portion of the angled end 39 of the shield 30 (which is relatively flexible compared to the deflector 80) to reach and directly abut the bottom surface 112 of the table 110 and thus to act as a "sweeper" along the bottom surface 112 of the table 110. In particular, this upper portion of the angled end 39 of the shield 30 may bend above the vertical portion 92 of the deflector 80 and along where the shield 30 contacts the bottom surface 112 of the table 110, thereby sealing to the bottom surface 112 of the table 110 and ensuring better shielding. Accordingly, as shown in FIG. 10, the height SH of the vertical portion 92 of the deflector 80 is less than the height of the angled end 39 of the shield 30 (above the body 37 of the shield 30). According to one embodiment, the height of the angled end 39 of the shield 30 may be approximately 2.5 to 3 inches, and the height SH of the vertical portion 92 of the deflector 80 may be approximately 1.0 to 1.5 inches.

In order to provide adequate support to the end portion of the shield 30 and to the vertical shield 84, the deflector 80 is relatively more stiff than the shield 30 (which may be flexible enough to easily bend). For example, the upper support element 82 and the lower support element 86 may be constructed out of a variety of different materials, including but not limited to carbon fiber.

In order to provide additional vertical shielding and to attenuate the scatter radiation 123, the deflector 80 may include a vertical shield 84 (as shown in FIG. 10) that is positioned between the respective vertical portions 92 of the upper support element 82 and the lower support element 86 of the deflector 80. The vertical shield 84 may optionally be positioned between layers of at least a portion of the angled end 39 of the shield 30. The vertical shield 84 may be constructed out of a variety of different rigid radiation-shielding materials that are radiopaque, such as copper, and both support the shield 30 and further attenuate x-rays. The vertical shield 84 may include multiple layers for additional support and shielding. According to one embodiment, the vertical shield 84 may only extend within the vertical portion 92 of the deflector 80 (and not the horizontal portion 94 of the deflector 80). According to another embodiment, the vertical shield 84 may optionally also extend at least partially along the horizontal portion 94 of the deflector 80.

According to one embodiment, the vertical shield 84 may extend vertically above the respective vertical portions 92 of the upper support element 82 and the lower support element 86. Accordingly, the height HS of the vertical shield 84 may be greater than the height SH of the respective vertical portions 92 of the upper support element 82 and the lower support element 86 (as shown in FIG. 10). Alternatively, the heights HS and SH may be approximately the same, depending on the desired configuration. For example, the height HS of the vertical shield 84 may be approximately 1.0 to 1.5 inches, and the height SH may be approximately 1.0 to 1.5 inches. However, the vertical shield 84 may be shorter than and may not extend along the entire height of the angled end 39 of the shield 30 (in particular the upper portion of the angled end 39) in order to allow the upper portion of the angled end 39 of the shield 30 to be flexible and bend along the bottom surface 112 of the table 110. Furthermore, the vertical shield 84 may be more narrow than the angled end 39 of the shield 30 (in particular above the notches 88) and may not extend along the flap 97 of the shield 30. Additionally, according to one embodiment, the vertical shield 84 may optionally be approximately 0.10 inches thick.

According to one embodiment as shown in FIG. 10 and as described further herein, a lower portion of the angled end 39 of the shield 30 may have an indentation or notch 88 in order to prevent the lower portion of the angled end 39 of the shield 30 from hitting the table mounts 157 (i.e., a suction mount 60 and/or a clamp mount 160), the mount supports 167, or the mount bracket 62 as the shield 30 is moved along the length of the rail assembly 50. The top portion of the angled end 39 of the shield 30 (which is above the notch 88) may be sufficiently high to vertically clear the mount supports 167 and therefore may not need a reduced length (unlike the bottom portion of the angled end 39 of the shield 30). Accordingly, the length of the top portion of the angled end 39 of the shield 30 (and the width WS of the horizontal portion of the shield 30, as shown in FIG. 4) is greater than the length of the bottom portion of the angled end 39 of the shield 30 (where the bottom portion of the vertical portion of the shield 30 directly connects to the body 37 of the shield 30), which creates the notch 88. Accordingly, with the reduced lower width along the lower portion of the angled end 39 of the shield 30 (i.e., at the notch 88), the shield 30 can clear and move past the table mounts 157 without any interference.

Since the upper portion of the angled end 39 of the shield 30 has a greater width than the lower portion of the angled end 39 of the shield 30 to form the notch 88, flaps 97 of the shield 30 are formed above the notch 88, which maximizes the amount of shielding. The flaps 97 extend horizontally beyond the length of the vertical portion 92 of the deflector 80 (including any vertical shield 84 and along both ends of the vertical portion 92 in the direction of the width of the shield 30) and vertically above the height of the notch 88 and the height HS of the vertical portion 92 of the deflector 80 (including any vertical shield 84). According to another embodiment, the shield 30 may not include the notch 88, and the flaps 97 may be defined by a horizontal slit in the angled end 39 of the shield 30. Accordingly, the flaps 97 may move independently in the direction of movement of the shield 30 along the rail assembly 50 relative to the rest of the shield 30 (i.e., the body 37 and the rest of the angled end 39) and the deflector 80.

Alternatively or additionally, as shown in FIG. 10, the vertical portion 92 of the deflector 80 may have a reduced lower width (relative to the horizontal portion 94 of the deflector 80) such that the deflector 80 does not hit the table mounts 157 or the mount supports 167. For example, the length of the vertical portion 92 of the deflector 80 (which may be approximately equal to or less than the length of the bottom portion of the angled end 39 of the shield 30 along the notch 88) may be less than the length of the top portion of the angled end 39 of the shield 30 along the flaps 97 and less than the length of the horizontal portion 94 of the deflector 80. Accordingly, the deflector 80 can clear and move past the table mounts 157 and the mount supports 167 without any interference. The horizontal distance between the end of the one of the flaps 97 and the nearest end of the horizontal portion 94 of the deflector 80 may be approximately 2.0 inches.

According to one embodiment, the angled end 39 of the shield 30 may not include the notch 88 and may extend horizontally beyond the ends of the vertical portion 92 of the deflector 80. Accordingly, the angled end 39 of the shield 30 may have a substantially constant length along the height of the angled end 39. In this embodiment, the bottom portion of the angled end 39 extends horizontally beyond the ends of the vertical portion 92 of the deflector 80 (along the length).

The various portions of the deflector 80 may have a variety of different dimensions according to the desired configuration. According to one embodiment, the width SW of the horizontal portion 94 of one of the upper support element 82 or the lower support element 86 of the deflector 80 (as shown in FIG. 10) may be approximately 1.0 inches. According to one embodiment, the length of the horizontal portion 94 of the deflector 80 (which may correspond to the width WS of the shield 30) may be approximately 18 inches, the length of the vertical portion 92 of the deflector 80 may be approximately 14 inches (or alternatively approximately 13 inches), and therefore, the horizontal portion 94 extends approximately 2 inches (or alternatively approximately 2.5 inches) horizontally beyond the vertical portion 92 on each side of the deflector 80.

The length of the angled end 39 of the shield 30 above the end of the vertical portion 92 of the deflector 80 (i.e., along the flaps 97) may be shorter than the length of the horizontal portion 94 of the deflector 80 in order to horizontally clear the rails 51. For example, the length of the shield 30 along the flaps 97 may be approximately 14-16 inches.

Alternatively or additionally, the radiation shield assembly 20 may include a flat support element 98 positioned along the body 37 of the shield 30 at the end of the shield 30 (along the length of the shield 30), as shown in FIG. 4. The support element 98 further supports the shield 30 and may be positioned along an opposite end of the shield 30 as the deflector 80. The shield 30 may or may not include an angled end 39 along the end of the shield 30 that includes the flat support element 98 (rather than the deflector 80). The support element 98 may be constructed out of a variety of different materials, including but not limited to carbon fiber. According to one embodiment, the flat support element 98 may have a width of approximately 1 inch and a thickness of approximately ⅛ inch. The length of the support element 98 may correspond to the width WS of the shield 30. Accordingly, the length of the support element 98 may be approximately 10-30 inches, more preferably 15-25 inches, or most preferably 18 inches.

Locking Handle

Figure 11A:
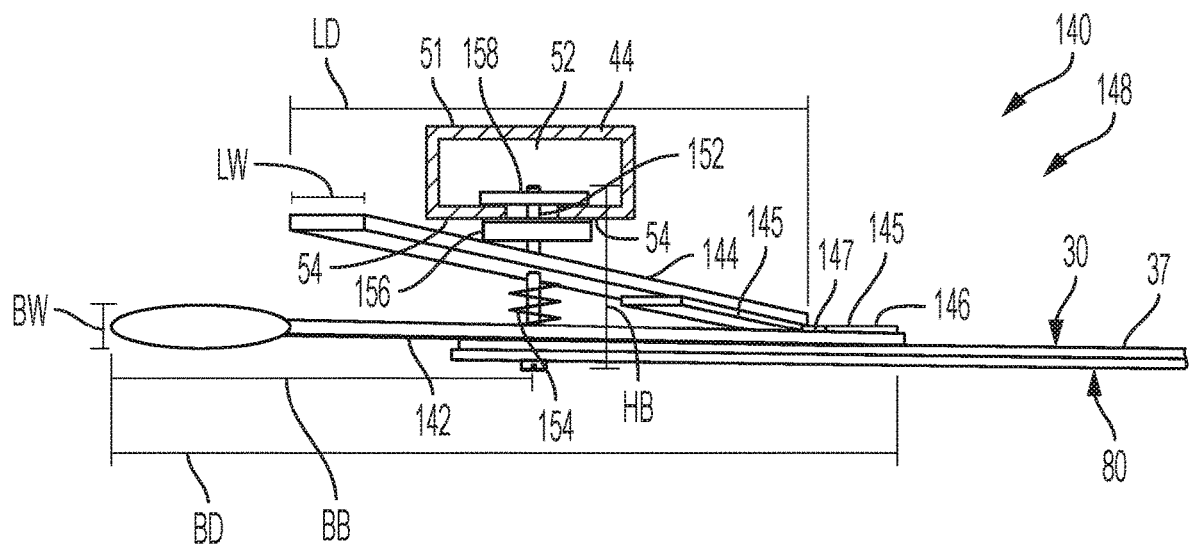
FIG. 11A is a side, cross-sectional view of a handle of the radiation shield assembly of FIG. 3 in a locked position.
Figure 11B:
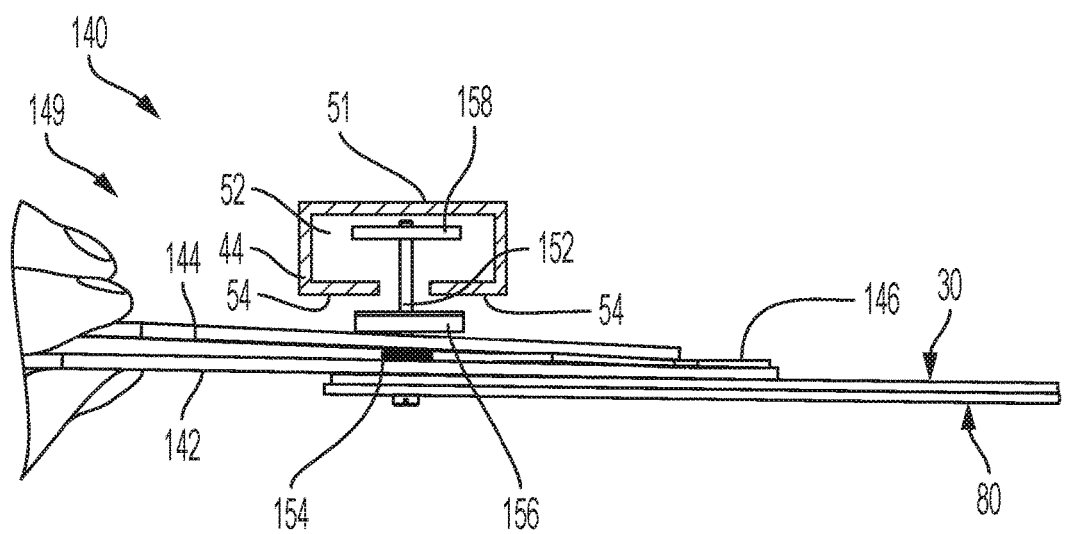
FIG. 11B is a side, cross-sectional view of the handle of the radiation shield assembly of FIG. 3 in an unlocked position.

As shown in FIGS. 4 and 11A-11B, the radiation shield assembly 20 may include a locking mechanism (which may be and is referred to herein as a locking handle 140) that is configured to lock the shield 30 in any position (i.e., in the retracted position 32, in the extended position 36, or in a position between the retracted position 32 and the extended position 36 (i.e., the partially extended position 34)). Furthermore, the handle 140 is configured to move (e.g., push or pull) the shield 30 along the length of the rails 51 such that the shield 30 covers or exposes certain areas or to adjust the field of view at any time.

The handle 140 includes a locking, stopping, or braking system, mechanism, or assembly in order to lock the shield 30 in a particular position along the length of the rails 51. Accordingly, the handle 140 is movable between a braked or locked position 148 (as shown in FIG. 11A) in which the handle 140 is locked and the shield 30 is not movable along the length of the rail 51 and a movable, released, or unlocked position 149 (as shown in FIG. 11B) in which the handle 140 is unlocked and the shield 30 is movable along the length of the rail 51.

As shown in FIG. 11A, the handle 140 includes a base 142, a lever 144, and a hinge 146. The hinge 146 movably or pivotably attaches the back end of the lever 144 to the base 142 such that the front end of the lever 144 can pivot relative to the base 142. By moving the lever 144 up and down relative to the base 142, the user may move the handle 140 between the locked position 148 and the unlocked position 149. More specifically, by moving the lever 144 toward the base 142, the handle 140 is moved into the unlocked position 149. When the user releases the lever 144, the handle 140 automatically moves away from the base 142, thereby moving back into the locked position 148.

As further shown in FIG. 11A, the handle 140 further includes a fastener (e.g., a screw, pin, or bolt 152), a spring 154, a lower brace (referred to herein as a lower washer 156), and an upper brace (referred to herein as an upper washer 158) in order to automatically move the handle 140 from the unlocked position 149 toward the locked position 148. The bolt 152 extends substantially vertically through holes in both the base 142 and the lever 144 in a middle portion along the lengths of the base 142 and the lever 144. The bolt 152 may further extend through the shield 30 and optionally a rod 40, the horizontal portion 94 of the deflector 80, or the flat support element 98 (all of which would be positioned beneath the base 142, on the opposite side as the lever 144) in order to attach the handle 140 to the shield 30 and to allow the handle 140 to control the position of the shield 30. The base 142 is statically attached to the lower portion of the bolt 152, and the lever 144 is movably attached to a middle portion of the bolt 152 (and is movable along the length of the bolt 152).

The spring 154 is positioned around the bolt 152 and between the lower surface of the lever 144 and the upper surface of the base 142 and provides resistance against moving the lever 144 away from the rail 51, which biases the handle 140 toward the rail 51 and toward the locked position 148 and automatically locks the handle 140 in position to the rail 51 (when the user releases the handle 140). The spring 154 pushes the lever 144 away from the base 142 and toward the locked position 148. Accordingly, the handle 140 is biased toward the locked position 148.

The lower washer 156 and the upper washer 158 are each positioned around the bolt 152 and above the upper surface of the lever 144 (along the length of the bolt 152). The lower washer 156 is positioned next to the upper surface of the lever 144, and the upper washer 158 is positioned above and spaced apart from the lower washer 156 along the length of the bolt 152 (e.g., toward the top of the bolt 152). As shown in FIGS. 11A-11B, the upper washer 158 is positioned within the slot 52 of the rail 51 (movable and securable along the upper surface of the lips 54 of the rail 51) and holds or secures the top or end of the bolt 152 within the slot 52 (and the lips 54 retain the upper washer 158 within the slot 52). The lower washer 156 is positioned outside of and below the slot 52 of the rail 51 (movable and securable along the lower surface of the lips 54 of the rail 51). Accordingly, the lips 54 of the rail 51 are sandwiched between the upper washer 158 and the lower washer 156 (and thus the lever 144) for a secure attachment. The upper washer 158 slides within and along the length of the slot 52 (which allows the rest of the handle 140 to move with the upper washer 158 along the rail 51) when the handle 140 is in the unlocked position 149 and being moved. According to another embodiment, the handle 140 may not include the lower washer 156, and instead the lever 144 may be the lower brace.

In order to lock the handle 140 to the rail 51, the lower washer 156 and the lever 144 are movable along the length of the bolt 152. The upper washer 158 and the base 142, however, are statically attached to opposite ends of the bolt 152. Accordingly, in the locked position 148 (as shown in FIG. 11A), the spring 154 is presses the lever 144 and the lower washer 156 away from the base 142 and toward the bottom surface of the lips 54 of the rail 51 and the upper washer 158. Accordingly, the spring 154 compresses or pinches the lips 54 of the rail 51 between the upper washer 158 and the lower washer 156 (and the lever 144) when the handle 140 is released by the user (or when the user is not compressing the handle 140), which prevents the upper washer 158 from moving along the length of the rail 51 and brakes and locks the handle 140 (and the shield 30).

In order to unlock the handle 140, the user may press the lever 144 toward the base 142 until the handle 140 is moved into the unlocked position 149, thereby releasing the grip on the lips 54 of the rail 51, as shown in FIG. 11B. In the unlocked position 149, the user overcomes the force of the spring 154 and thereby moves the lever 144 relatively close to the base 142, away from the rail 51. This action compresses the spring 154 between the lever 144 and the base 142 and allows the lower washer 156 to move away and separate from the lips 54 of the rail 51 and the upper washer 158 along the bolt 152, which releases the lips 54 of the rail 51 and allows the lower washer 156 and the upper washer 158 (and thus the entire handle 140) to move relative to the lips 54 of the rail 51. Accordingly, in the unlocked position 149, there is a larger gap between the upper washer 158 and the lower washer 156 along the length of the bolt 152, which allows the upper washer 158 to move and slide freely within the slot 52 of the rail 51 and along the length of the top surface of the lips 54 of the rail 51. The rest of the handle 140 moves with the upper washer 158 along the rail 51 in the unlocked position 149. Accordingly, in order to move the shield 30 back and forth along the length of the rail assembly 50, the user may grasp the handle 140, push the lever 144 toward the base 142 (which moves the handle 140 into the unlocked position 149), and, while the lever 144 is still pushed toward the base 142, move the handle 140 along the rail assembly 50.

According to one embodiment, the upper washer 158 may be in contact with the rail 51 in both the locked position 148 and the unlocked position 149, while the lower washer 156 may only be in contact with the rail 51 in the locked position 148.

The handle 140 may be positioned in a variety of different places along the length of the shield 30. As shown in FIGS. 1-4, the handle 140 may be positioned toward or at an end of the shield 30 (along the length of the shield 30) (on, for example, the horizontal portion 94 of the deflector 80, as shown in FIG. 11A). The front ends of the base 142 and the lever 144 may extend out beyond the shield 30 (along the width of the shield 30) to allow the user to easily access and use the handle 140 (where the base 142 and the lever 144 are movably attached to each other through their respective back ends). Optionally, multiple handles 140 may be attached to the shield 30 (such as at opposite ends of the shield 30) in order to control and secure the position of both ends of the shield 30.

The various components of the handle 140 may be constructed out of a variety of materials. For example, according to one embodiment, the base 142 and the lever 144 may each be constructed out of carbon fiber. The lower washer 156 may be constructed out of rubber (in order to, for example, firmly grip the bottom surface of the lips 54 of the rail 51 and prevent the handle 140 from sliding in the locked position 148). The upper washer 158 may be constructed out of nylon or Teflon (in order to, for example, easily slide along the top surface of the lips 54 of the slot 52 in the unlocked position 149). Since nylon has a relatively low friction with carbon fiber, the nylon upper washers 158 may slide relatively easily along the rail 51. Furthermore, since nylon has a relatively low coefficient of friction, the nylon upper washers 158 are more resistant to wear.

The hinge 146 may be constructed out of a variety of different materials in order to movably attach the base 142 and the lever 144. For example, the hinge 146 may include two support portion 145 and a flexible portion 147 (where the support portions 145 are positioned on opposite sides of the flexible portion 147). The support portion 145 is relatively stiff and securely attaches to the base 142 or the lever 144 (with, for example, an adhesive). The flexible portion 147 is relatively flexible and bendable and is positioned in between the two support portions 145. The flexible portion 147 flexes and bends as the two support portions 145 are moved relative to each other (and thus as the lever 144 moves relative to the base 142).

According to one embodiment, the support portions 145 are constructed out of carbon fiber, and the flexible portion 147 is constructed out of ballistic Kevlar, which allows the hinge 146 to be ultralight and low profile. Furthermore, the hinge 146 does not have to include any fasteners (such as bolts) to attach to the base 142 or the lever 144 and may only use, for example, an adhesive to attach to the base 142 and the lever 144. The material of the flexible portion 147 may optionally extend into either or both of the support portions 145 (and thus be sandwiched between layers of carbon fiber in each of the support portions 145) in order to increase the strength of the hinge 146. According to another embodiment, however, the hinge 146 may be constructed out of metal.

The handle 140 may have a variety of different dimensions according to the desired configuration. For example, the diameter of the upper washer 158 may be larger than the width of the longitudinal opening 46 into the slot 52 between the lips 54 to prevent the upper washer 158 from falling out of the slot 52 and may also be smaller than the width of the slot 52 to allow the upper washer 158 to move along the slot 52. According to one embodiment, the upper washer 158 may be an approximately ½ by ⅛ inch washer. The lower washer 156 may be an approximately ½ by 1/16 inch washer (which may be larger than the width of the longitudinal opening 46 to the slot 52 to prevent the lower washer 156 from moving into the slot 52).

As shown in FIG. 11A, the length BD of the base 142 may be approximately 8.5 inches and the longitudinal distance LD between the ends of the lever 144 when the lever 144 is angled relative to the base 142 (e.g., toward or in the locked position 148) may be approximately 6.0 inches. The distance BB between the bolt 72 and the front end of the base 142 may be approximately 5.2 inches. The width LW of the front end of the lever 144 may be approximately 0.90 inches, and the width BW of the front end of the base 142 may be approximately 1.8 inches. The height HB of the bolt 152 may be approximately 1.25 inches.

According to one embodiment, the roller structure 73 (as shown and described further herein) may be integrated into the handle 140 along the length of the bolt 152 (above the lower washer 156), thereby functioning as the upper brace and replacing the upper washer 158. The handle 140 may otherwise move and be operated in a similar manner with the roller structure 73.

Alternatively or additionally, as shown in FIG. 4, the radiation shield assembly 20 may include a non-locking handle 138 on either end (or both ends) of the shield 30 to allow the practitioner to grasp and easily move or slide the shield 30 along the length of the rails 51 to cover or expose certain areas or adjust the field of view at any time. The handle 138 may be constructed out of a variety of different materials, including but not limited to carbon fiber and may also be radiotranslucent.

Table Mounts

Figure 13B:
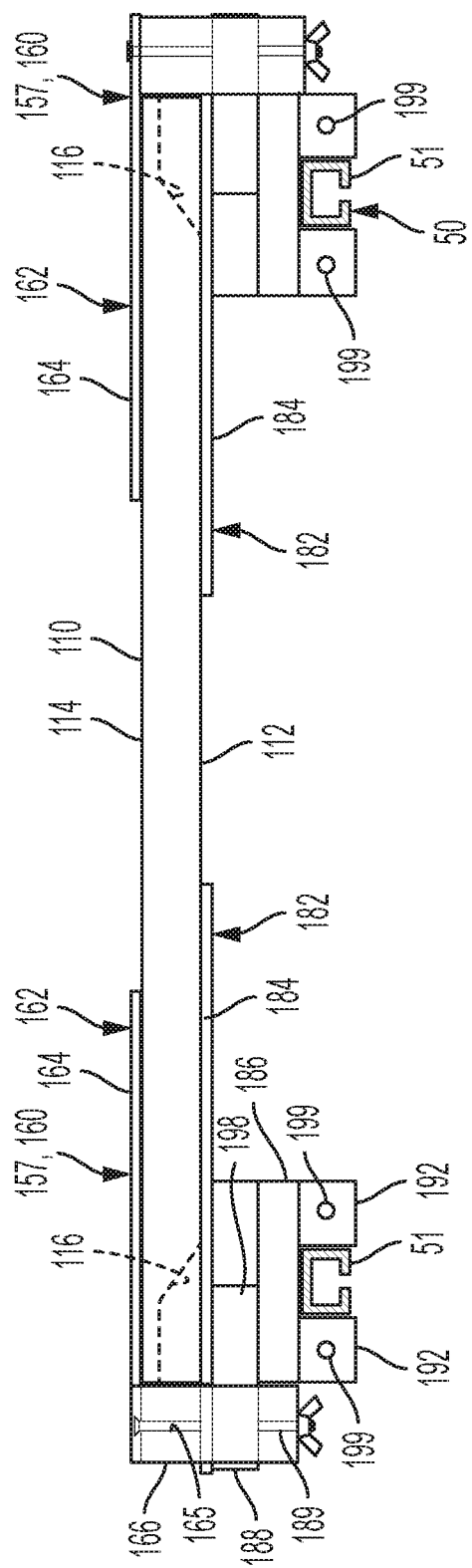
FIG. 13B is a cross-sectional view of the radiation shield assembly and table of FIG. 13A.
Figure 14:
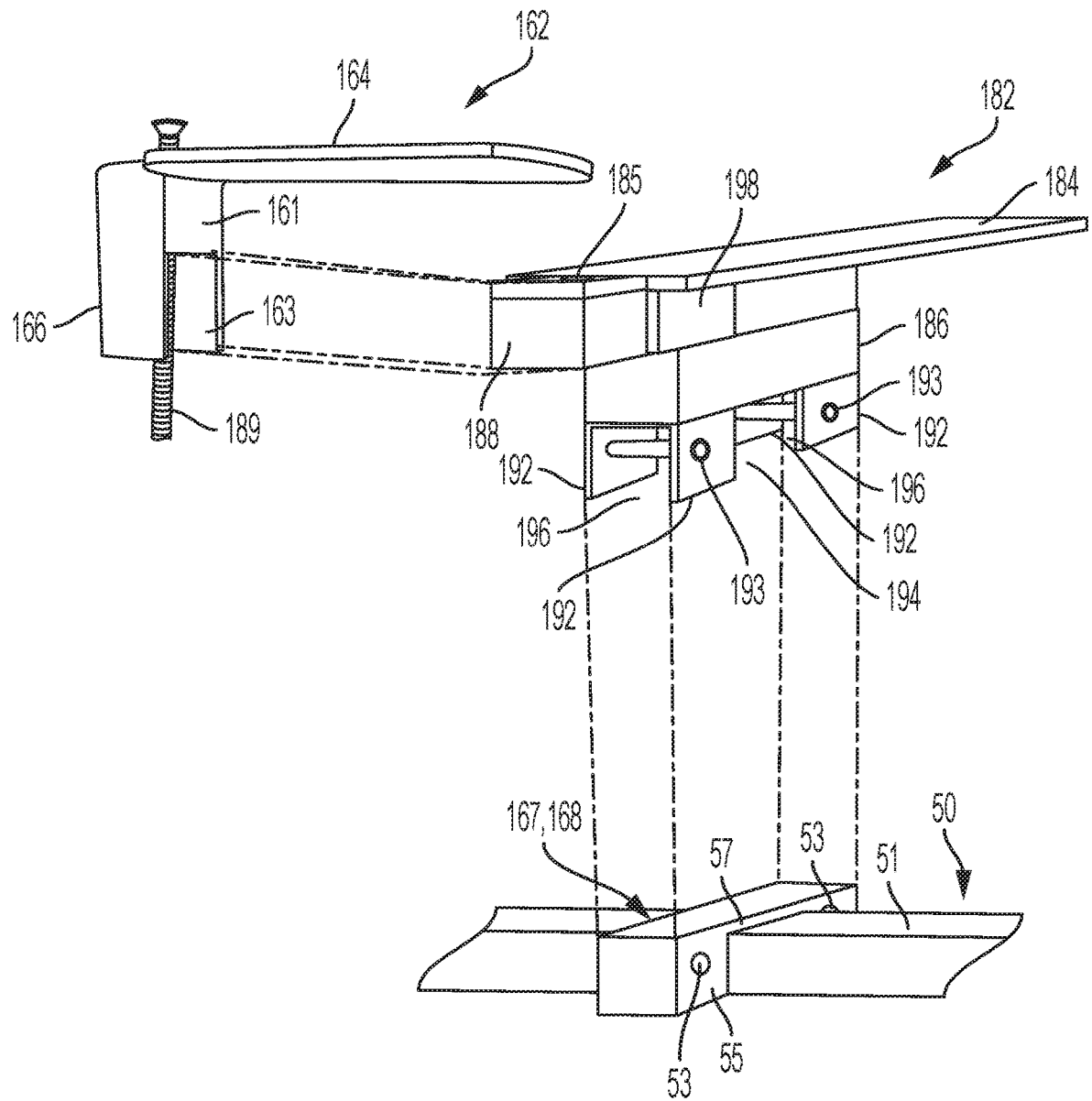
FIG. 14 is an exploded, perspective view of the clamp mount and rail assembly of FIG. 13A.

In order to attach the radiation shield assembly 20 to the table 110, the radiation shield assembly 20 may include table mounts 157 that are configured to removably and reattachably attach or mount the rail assembly 50 to the table 110 and hold the rest of the radiation shield assembly 20 in place relative to the table 110, as shown in FIGS. 12-14. As described further herein, the table mounts 157 allow the rest of the radiation shield assembly 20 to be attached to the table 110 without any modifications to the table 110 and without requiring the table 110 to be modified in any way. The table mounts 157 allow the radiation shield assembly 20 to be temporarily attached to, removed from, and reattached to various different tables 110 (which may have different sizes and/or shapes).

The table mounts 157 allow the radiation shield assembly 20 to universally and stably attach or mount to numerous different types, shapes, sizes, and configurations of tables 110. The table mounts 157 may allow the radiation shield assembly 20 to be easily retro-fitted to an existing table 110.

The table mounts 157 may allow the radiation shield assembly 20 (in particular the rail assembly 50) to be quickly and easily attached or secured to and released or removed from the table 110 with minimal effort and little training of the practitioner. Furthermore, the table mounts 157 do not require any modifications (e.g., hardware modifications or mechanism modifications), alterations, or mechanical fastening (e.g., bolting or screwing) to the radiation system or table 110 in order to attach the radiation shield assembly 20 (in particular the rail assembly 50) to the table 110. It may be necessary to completely remove the radiation shield assembly 20 in order to calibrate the radiation source 120. Therefore, it is highly beneficial that the table mounts 157 allow the radiation shield assembly 20 to be easily attached to, removed from, and reattached to the table 110. Additionally, the table mounts 157 can be attached to tables 110 with a variety of different widths and with or without tapers (particularly along the bottom surface 112 of the table 110, as shown, for example, in FIG. 13B and described further herein). Accordingly, the table mounts 157 can be attached to tables from a variety of different brands.

Different types of table mounts 157 may be used, depending on the desired configuration and the desired mounting configuration. For example, the table mount 157 may be a suction table mount structure (referred to herein as a suction mount 60 and as shown in FIGS. 12-13A) or a clamping table mount structure (referred to herein as a clamp mount 160 and as shown in FIGS. 13A-14), as described further herein.

The radiation shield assembly 20 may include any number of table mounts 157 according to various embodiments, such as four to six table mounts 157. Optionally, the radiation shield assembly 20 may utilize the same type or multiple different types of table mounts 157 (i.e., the clamp mounts 160 and/or the suction mounts 60) at the same time in order to attach to the table 110 in different manners, depending on the desired configuration. For example, according to one embodiment, the radiation shield assembly 20 may include and use only clamp mounts 160 (in particular four clamp mounts 160) in order to attach to the table 110. According to another embodiment as shown in FIG. 13A, the radiation shield assembly 20 includes and uses both clamp mounts 160 and suction mounts 60 (in particular two clamp mounts 160 at one end of the rail assembly 50 and two suction mounts 60 at the other end of the rail assembly 50) in order to attach to the table 110.

As shown in FIGS. 12-13A, the table mounts 157 may be attached to various portions of the rail assembly 50. The positioning of the table mounts 157 along the rail assembly 50 can be varied in order to maximize the stability of the radiation shield assembly 20 under a wide range of differently sized tables 110. For example, the table mounts 157 may be positioned at different points along the length of the rail assembly 50 (optionally toward the center along the length of the rail assembly 50), extending out from (substantially perpendicularly both above and along the width of) the rails 51. Alternatively or additionally, the table mounts 157 may be positioned at the ends of the rail assembly 50 (e.g., beneath the patient's head or feet and toward the center along the width of the rail assembly 50), extending from and attached to mount supports 167 positioned along a cross-beam 56 at the end of the rail assembly 50, as shown in FIG. 13A.

The table mount 157 may be configured to attach to the mount support 167 of the rail assembly 50. If the table mount 157 is attached to a mount support 167 of the rail assembly 50 (or to a mount bracket 62, which is attached to a mount support 167), the positioning of the table mount 157 depends on the positioning of the mount supports 167. Alternatively, the table mount 157 may be attached directed to the rail 51 or the cross-beam 56 of the rail assembly 50. For example, the table mount 157 may be positioned toward and attached to (and extend from) the edges or each end of the rail assembly 50 (in addition to or alternative to table mounts 157 that are attached to the mount supports 167).

Similar to the rail assembly 50, the table mounts 157 may also be constructed out of a material (or materials) that does not block or otherwise materially affect radiation 122 and is radiotranslucent (such that x-rays pass through the rail assembly 50), radiotransparent, or radiolucent in order to prevent any interference of the table mounts 157 with the radiation 122 that is intended to enter the patient 10 for examination purposes and to prevent any interference that may affect the imaging of the patient's body. For example, the table mounts 157 may be constructed out of carbon fiber, which is radiotranslucent. Accordingly, the table mounts 157 will not obstruct the practitioner's field of view while the radiation shield assembly 20 in place and will allow the practitioner to still completely visualize the patient without the table mounts 157 blocking or impeding any of the view (in particular while the shield 30 is in the retracted position 32 or the partially extended position 34), even if a portion of the table mounts 157 is within the field of view and the direct radiation beam 121 of the radiation 122.

Suction Mount

The suction mounts 60 (one type of the table mounts 157, as shown in FIGS. 12-13A) are configured to removably attach, suction, or mount underneath the table 110 (i.e., to the bottom surface 112 of the table 110, as shown in FIG. 12) with suction in order to attach the rest of the radiation shield assembly 20 (in particular the rail assembly 50) to the table 110. By mounting the radiation shield assembly 20 to the bottom surface 112 of the table 110, the radiation shield assembly 20 can be easily and quickly set up and mounted to the table 110. When the suction mount 60 is suctioned to the bottom surface 112 of the table 110 (and the radiation shield assembly 20 is assembled), the shield 30 and the rail assembly 50 are positioned along and below the bottom surface 112 of the table 110.

As shown in FIG. 12, the suction mounts 60 each comprise a suction cup 67 that suctions to the bottom surface 112 of the table 110 (or any other type of smooth surface). The suction cups 67 may be, for example only, 3.25 inch suction cups. The suction cups 67 may be, for example only, mechanical suction cups with rotating mounts.

In order to ensure that the suction cups 67 securely attach to the bottom surface 112 of the table 110, the radiation shield assembly 20 (in particular the suction mounts 60) may include stickers that are configured to adhere to the bottom surface 112 of the table 110. The stickers provide a smooth surface or area for the suction cups 67 to securely suction to and to create an airtight seal with. The stickers may be particularly beneficial if the table 110 is carbon fiber (and therefore porous and/or including microridges), which may otherwise prevent the suction cups 67 from creating a complete suction and thus prevent the suction cups from securely attaching to the table 110. The stickers may be, for example, polypropylene, polyvinyl, or PVC plastic with an adhesive backing and may be approximately 6 inches in diameter. The size and shape of the stickers may correspond to the size and shape of the suction cups 67 such that the stickers are approximately the same size or greater in size than the suction cups 67. According to one embodiment, the stickers are each approximately a 4 by 4 inch or 4 by 6 inch rectangle.

The suction mounts 60 each also comprise a suction cup holder 68 that secures to the suction cup 67 and attaches the suction cup 67 to the rail assembly 50 (through the mount support 167 and optionally the mount bracket 62). Accordingly, the suction cup holder 68 may be directly and pivotably attached to the rail assembly 50, to one of the mount supports 167, or to a mount bracket 62 (as described further herein) (as shown in FIG. 12). In order to attach to each of these components, the suction cup holder 68 includes at least one protrusion or extension 69 and a hole extending through the extension 69. For example, the suction cup holder may include two substantially parallel extensions 69, each of which include and define a hole extending completely through the extensions 69. According to one embodiment, the extensions 69 may extend along opposite sides of the mount bracket 62 (or, alternatively, along opposite sides of a portion of a rail 51, a cross-beam 56, or the mount support 167). However, according to another embodiment, the extension(s) 69 may extend into a portion of the mount bracket 62, the rail 51, the cross-beam 56, or the mount support 167.

The extensions 69 (in particular their respective holes) are aligned with each other and are configured to receive a fastener (e.g., a pin or bolt 61). The bolt 61 extends through the hole(s) in the extensions 69 of the suction cup holder 68 and through corresponding holes in the rail 51 (or in the cross-beam 56), in the mount support 167, or in the mount bracket 62 (depending on the desired configuration) in order to movably or rotatably attach the suction cup holder 68 (with the suction cup 67) to the rail 51 (or the cross-beam 56), the mount support 167 (as shown in FIG. 13A), or the mount bracket 62 (as shown in FIG. 12). A pivot axis may be formed through the centers of the holes in the extensions 69 of the suction cup holder 68 and the respective hole(s) in the rail 51 (or the cross-beam 56), the mount support 167 or the mount bracket 62, which allows the angle of the suction cup holder 68 (and thus the suction cup 67) to be changed relative to the rail 51 (or the cross-beam 56), the mount support 167, or the mount bracket 62.

According to one embodiment, the suction cup holder 68 is movably or rotatably attached directly to the rail 51. Accordingly, the rails 51 may each have a hole through which the suction cup holder 68 is directly attached to the rail 51. According to one embodiment, the hole in the rail 51 may be approximately 0.5 inches from each longitudinal end of each rail 51 and a ⅛ inch drilled hole. The suction cup holder 68 may be attached to the cross-beam 56 in a similar manner (and the cross-beam 56 may include similar hole(s)).

According to one embodiment as shown in FIG. 13A, the suction cup holders 68 may be movably or rotatably attached directly to the mount supports 167 (in particular the one-sided extension 58). As described further herein, the mount supports 167 are statically attached to another portion of the rail assembly 50, such as a rail 51 or a cross-beam 56, and include hole(s) 53. Accordingly, the bolt 61 may extend through the hole(s) in the suction cup holder 68 and the hole(s) 53 in the mount support 167 in order to directly attach the suction cup holder 68 to the mount support 167.

According to another embodiment as shown in FIG. 12, the suction cup holders 68 may be movably or rotatably attached directly to the mount brackets 62 (as described further herein), which are movably or rotatably attached directly to the mount support 167 (as shown in FIG. 12). Accordingly, the mount support 167 indirectly supports the suction cup holder 68 through the mount brackets 62. In order to movably or rotatably attach directly the suction cup holders 68 to the mount brackets 62, the bolt 61 may extend through the hole(s) in the suction cup holder 68 and corresponding second set of hole(s) 64 in the mount bracket 62.

Although the mount bracket 62 is shown to be attached with the one-sided extension 58 in FIG. 12, the suction mount 60 (as well as the mount bracket 62) may be used with and attached to a variety of different types of mount supports 167, including the two-sided extension 168, depending on the desired configuration.

The radiation shield assembly 20 may include multiple suction cup holders 68 that are attached to the rail assembly 50 in different manners (i.e., directly to the rail 51 (or the cross-beam 56), directly to the mount support 167, and/or directly to the mount bracket 62) according to the desired configuration.

Mount Bracket for the Suction Mount

According to one embodiment as shown in FIG. 12, the radiation shield assembly 20 may further comprise at least one arm, extension, or mount bracket 62 that is configured to attach the suction mount 60 to the rail assembly 50. Accordingly, the mount bracket 62 is positioned between and movably or rotatably attached to both the mount support 167 and the suction mount 60 (in particular to the suction cup holder 68. The mount bracket 62 may optionally be a part of the rail assembly 50 or the mount support 167 and/or constructed in a similar manner and with similar materials as the rail assembly 50. The mount bracket 62 is particularly useful along the portion of the rail assembly 50 that corresponds to the head of the table 110.

The mount bracket 62 allows the suction mount 60 to be offset vertically and/or horizontally by greater distance from the mount support 167, and thus also from the rail 51 or the cross-beam 56 of the rail assembly 50 (compared to if the suction mount 60 were directly attached to the mount support 167, the rail 51, or the cross-beam 56). Furthermore, the mount bracket 62 allows the position of the suction mount 60 to be adjusted to a greater degree according to the user's needs and the dimensions or configuration of the particular table 110 that the radiation shield assembly 20 is being used with. Accordingly, the mount bracket 62 allows the radiation shield assembly 20 fit with a wider variety of different sized and shaped tables 110.

Since the mount bracket 62 can be angled away from the mount support 167, the suction mount 60 can be positioned at a different height than the mount support 167, the rail 51, and the cross-beam 56. Accordingly, the mount bracket 62 spaces the rail assembly 50 vertically away from the bottom surface 112 of the table 110.

Since the height of each of the suction mounts 60 can be individually adjusted via the mount brackets 62, the radiation shield assembly 20 may accommodate and adapt to various curvatures along the bottom surface 112 of the table 110. For example, the bottom surface 112 of the table 110 may not necessarily be flat. Instead, the bottom surface 112 of the table 110 may be curved, tapered, or angled upward at approximately 15° along the area underneath the head and/or shoulders of the patient 10. By adjusting the angle of each of the mount brackets 62 (and therefore height of the suction mounts 60) relative to the mount support 167 (and thus relative to the rails 51 and the cross-beam 56), the rail assembly 50 can be tailored to the specific configuration of the table 110 and therefore can be attached to a variety of different configurations of tables 110. According to one embodiment, the mount bracket 62 may raise the suction mount 60 up to approximately 2 inches above the rail 51 or the cross-beam 56.

In order to movably or rotatably attach to both the mount support 167 and the suction mount 60, the mount bracket 62 includes a first set of holes 63 and a second set of holes 64. The first set of holes 63 and the second set of holes 64 are positioned along opposite ends of the mount bracket 62. Accordingly, the mount bracket 62 provides double articulation with two pivot axes, wherein one pivot axis extends through the first set of holes 63 and the other pivot axis extends through the second set of holes 64. This configuration allows the vertical position (i.e., the height) and the horizontal position of the suction mount 60 to be adjusted relative to the rest of the rail assembly 50, and the angle of the suction cup 67 can be adjusted according to the desired angle (i.e., depending on the relative angle of the bottom surface 112 of the table 110).

The first set of holes 63 is configured to align with the holes 53 in the mount support 167, and a fastener (e.g., a pin or bolt 61) extends through the first set of holes 63 and the holes 53 in order to attach the mount support 167 and the mount bracket 62 together. The second set of holes 64 is configured to align with the holes in the suction mount 60 (in particular the suction cup holder 68), and another bolt 61 extends through the second set of holes 64 and the holes in the suction mount 60 in order to attach the suction mount 60 and the mount bracket 62 together.

As shown in FIG. 12, the mount bracket 62 comprises a body 66 and at least one extension or protrusion 65 (for example two parallel protrusions 65 extending from one end of the body 66). The body 66 may comprise a top wall, a bottom wall, and two side walls. The protrusions 65 extend from two opposite walls along a first end of the body 66 and define the first set of holes 63. The second end of the body 66 defines the second set of holes 64 (where the first end of the body 66 is opposite to the second end of the body 66 along the length of the mount bracket 62).

In order to attach the mount bracket 62 to the mount support 167, the first set of holes 63 in the mount bracket 62 are aligned with the holes 53 in the mount support 167 by, for example, positioning the protrusions 65 of the mount bracket 62 around opposite sides of the base 55 of the mount support 167 such that the protrusions 65 at least partially overlap the base 55 of the mount support 167 to align the holes. A bolt 61 is then moved into or through each of the respective holes in the mount bracket 62 and in the mount support 167. Since the protrusions 65 of the mount bracket 62 do not have top or bottom walls therebetween, the mount bracket 62 can move or pivot relative to the mount support 167 about a first pivot axis while the bolt 61 is positioned within the first set of holes 63 of the mount bracket 62 and the holes 53 in the mount support 167 in order to change the height and horizontal position of the suction mount 60 relative to the mount support 167 (and the rail 51 or the cross-beam 56).

In order to attach the mount bracket 62 to the suction mount 60, the holes in the extensions 69 of the suction cup holder 68 of the suction mount 60 may be aligned with the second set of holes 64 in the mount bracket 62 by, for example, positioning the extensions 69 of the suction cup holder 68 extends into the body 66 of the mount bracket 62 (or, alternatively, positioning the extensions 69 of the suction cup holder 68 around opposite sides of the body 66 of the mount bracket 62 such that the extensions 69 at least partially overlap the second end of the body 66 of the mount bracket 62) to align the holes. Another bolt 61 is then moved into or through each of the respective holes in the mount bracket 62 and the suction mount 60. Since the extension 69 of the suction mount 60 do not have top or bottom walls therebetween, the suction mount 60 can move or pivot relative to the mount bracket 62 about a second pivot axis while the bolt 61 is positioned within the holes in the suction mount 60 and the second set of holes 64 of the mount bracket 62 in order to change the angle of the suction mount 60.

The mount bracket 62 may have a variety of different dimensions according to the desired configuration. According to one embodiment, the protrusions 65 may extend directly from side walls of the mount bracket 62. According to another embodiment, the protrusions 65 may each be a sheet of material that at least partially overlaps the body 66 of the mount bracket 62. For example, according to one embodiment, the total length of the protrusions 65 (including the portion overlapping the body 66) may be approximately 2.60 inches, the length of the body 66 may be approximately 2.60 inches, and the protrusions 65 may each overlap a side of the body 66 by a length of approximately 1.75 inches. The total length of the mount bracket 62 may be approximately 3.4 inches.

The width of the mount bracket 62 may be approximately 1.05 inches and the distance between the inner sides of the protrusions 65 may be approximately 0.90 inches, which may be greater than the width of the mount support 167 such that the mount support 167 fits between the two protrusions 65. The width of a portion of the mount bracket 62 (of the bottom wall) may be approximately 0.73 inches. The height of the mount bracket 62 may be approximately 0.50 inches.

A tube or tubing may optionally extend through each of the first set of holes 63 and the second set of holes 64 of the mount bracket 62, connecting the two holes in each of the sets of holes 63, 64. According to one embodiment, the first set of holes 63 and the second set of holes 64 may be approximately the same size. For example, the inner diameter of the first and second sets of holes 63, 64 (or tubing) may be approximately 0.170 inches and the outer diameter of the tubing may be approximately 0.25 inches. The size of the first and second sets of holes 63, 64 may be correlated to the size of the holes 53 in the mount support 167 and the holes in the table mounts 157.

Clamp Mount

The clamp mounts 160 (another type of the table mounts 157, as shown in FIGS. 13A-14) are configured to removably attach, mount, or clamp to the table 110 (as shown in FIGS. 13A-13B) with a clamping force in order to attach the rest of the radiation shield assembly 20 to the table 110. In particular, the clamp mounts 160 are configured to clamp the top surface 114 and the bottom surface 112 of the table 110. Due to the configuration of the clamp mounts 160, as well as the two-sided extension 168, the weight of the radiation shield assembly 20 (in particular the shield 30, which may be constructed out of led) is fully supported, and the force of the weight is applied in the vertical direction, rather than a horizontal direction, which prevents torque from being exerted onto the rail assembly 50. Such torque on the rail assembly 50 may otherwise pull the rail assembly 50 at least partially out of shape or dimension, which may cause the shield adjuster 70 to bind within the rail 51, which would prevent the shield adjuster 70 (along with the shield 30) from being easily movable (or movable at all) along the length of the rail assembly 50.

As shown in FIGS. 13A-14, the clamp mounts 160 each comprise an upper clamp 162 and a lower clamp 182 (as described further herein) in order to clamp to and along both the top surface 114 and the bottom surface 112 of the table 110, thereby sandwiching and securing the table 110 between at least a portion of the upper clamp 162 and at least a portion of the lower clamp 182. Accordingly, as shown in FIGS. 3 and 13A-13B, the clamp mount 160 extends along both the top surface 114 and the bottom surface 112 of the table 110, as well as any side surface of the table 110 extending between the top surface 114 and the bottom surface 112. As described further herein, the clamp mounts 160 are each attached and rigidly secured (via the lower clamp 182) to the rail assembly 50 in order to secure the rest of the radiation shield assembly 20 to the table 110.

As shown in FIGS. 13A-13B, the clamp mount 160 (in particular the upper paddle 164 and the lower paddle 184, as described further herein) is positioned along the top of the rail assembly 50 (e.g., along and above the top wall 48 of the rail 51 that is opposite the longitudinal opening 46 leading to the slot 52 within the rail 51) such that the clamp mount 160 and the shield 30 are on opposite sides of the rail 51. With this arrangement, the clamp mount 160 does not interfere with movement of the shield 30 along the rail assembly 50. Accordingly, at least the lower paddle 184 of the clamp mount 160 is positioned between the rail assembly 50 and the table 110 (while at least a portion of the upper paddle 164 is positioned above the table 110).

As shown in FIGS. 13A-13B, at least a portion of the top or upper bracket or clamp 162 is configured to extend substantially along and secure the top surface 114 of the table 110. Accordingly, as shown in FIGS. 13A-14, the upper clamp 162 includes an upper paddle 164 and an upper base 166. The upper extension, plate, or paddle 164 is configured to extend horizontally beyond the upper base 166 and along (and parallel to) the top surface 114 of the table 110 toward a center portion of the table 110 (along the width or length of the table 110) and is on an opposite side of the table 110 as the lower paddle 184 of the lower clamp 182 (as described further herein). Accordingly, as shown in FIG. 13B, the upper paddle 164 is substantially flat along its length and width (i.e., relatively thin) in order to minimize how much the clamp mount 160 extends vertically above the table 110. The upper paddle 164 is substantially wide and long along its width and length in order to provide a relatively large surface contact area between the upper paddle 164 and the top surface 114 of the table 110 for a more secure attachment to the table 110.

The upper base 166 of the upper clamp 162 provides an area for the upper clamp 162 to attach to the lower clamp 182 (as described further herein). Accordingly, as shown in FIG. 13B, the upper base 166 extends in a substantially perpendicular manner to the upper paddle 164 in order to extend along a side or edge of the table 110 (that is between the top surface 114 and the bottom surface 112 of the table 110) and to reach and attach to the lower clamp 182.

As shown in FIG. 13B, the upper base 166 includes a hole 165 that extends substantially vertically through the upper base 166 and along the height of the upper base 166. The hole 165 is configured to receive at least a portion of a fastener (e.g., a pin, screw, or bolt 189) (and accordingly extends completely through the upper base 166 (including through the notch 163), as shown in FIGS. 13B-14) in order to attach to the lower clamp 182. The bolt 189 may be, for example only, a ¼ by 20 bolt.

According to one embodiment as shown in FIG. 14, the upper base 166 includes two opposing side walls and a back wall and a top wall that defines the hole 165. The side walls and the back wall each extend along the height of the upper base 166 and define the notch 163 of the upper base 166. The upper paddle 164 may be in line with and extend directly from the top wall. The upper base 166 may be substantially hollow (along the notch 163) and does not include a front wall (opposite the back wall) or a bottom wall (opposite the top wall) in order to allow a portion of the side walls and the back wall to extend around a portion of the lower clamp 182 (in particular the horizontal extension 188 of the lower clamp 182). Accordingly, the upper base 166 has a hollow portion or notch 163 (as shown in FIG. 14) that extends between the bottom of the upper base 166 to the bottom surface of the upper paddle 164 of the upper clamp 162 and is configured to receive the horizontal extension 188 of the lower clamp 182.

According to another embodiment as shown in FIG. 14, a portion of the upper base 166 (that is above the notch 163) may be filled in (with, for example, epoxy) in order to increase the strength of the upper base 166, to provide an area to rest on a top surface of the lower clamp 182, and to act as a guide and thus prevent any pivoting between the upper clamp 162 and the lower clamp 182. This filled-in portion defines a front wall 161 of the upper base 166 that extends along only a portion of the height of the upper base 166 that is above the notch 163 and is configured to directly contact and extend along a side or edge of the table 110 once assembled to the table 110 (where this edge of the table 110 extends between the top surface 114 and the bottom surface 112 of the table 110). The front wall 161 extends between a bottom surface of the upper paddle 164 and an approximately middle portion along the height of the upper base 166 (i.e., the top of the notch 163). Accordingly, the notch 163 extends between the bottom of the front wall 161 and the bottom of the entire upper base 166. The hole 165 may extend completely through this filled-in portion and along the entire height of the front wall 161 and may optionally include tubing to further define the hole 165 within the filled-in portion of the upper base 166.

The upper clamp 162 may have a variety of different dimensions according to the desired configuration. According to one embodiment, the total length of the entire upper clamp 162 may be approximately 6 to 8.5 inches, and the length of the upper base 166 may be approximately 1 to 1.25 inches (e.g., approximately 1.10 inches). The thickness of the upper paddle 164 may be approximately 0.15 inches. The width of the upper paddle 164 may be approximately 2.50 inches, and the width of the upper base 166 may be approximately 1.25 inches.

As shown in FIGS. 13A-13B, at least a portion of the bottom or lower bracket or clamp 182 is configured to extend substantially along and secure and support the bottom surface 112 of the table 110. Additionally, the lower clamp 182 is configured to fix the entire clamp mount 160 (and thereby also the table 110) to the rail assembly 50. Accordingly, as shown in FIG. 14, the lower clamp 182 includes a lower paddle 184 and a lower base 186. The lower extension, plate, or paddle 184 is configured to extend horizontally beyond the lower base 186 and along (and parallel to) the bottom surface 112 of the table 110 toward a center portion of the table 110 (along the width or length of the table 110) and is on an opposite side of the table 110 as the upper paddle 164 of the lower clamp 182 (as described further herein). Accordingly, as shown in FIGS. 13B-14, the lower paddle 184 is substantially flat along its length and width (i.e., relatively thin) in order to minimize how much the clamp mount 160 extends vertically below the table 110. The lower paddle 184 is substantially wide and long along its width and length in order to provide a relatively large surface contact area between the lower paddle 184 and the bottom surface 112 of the table 110 for a more secure attachment to the table 110. As shown in FIG. 13B, the lower paddle 184 and the upper paddle 164 are substantially parallel to each other such that the table 110 fits and is secured easily in between the lower paddle 184 and the upper paddle 164.

The lower base 186 of the lower clamp 182 provides an area for the lower clamp 182 to attach to the upper clamp 162 (as described further herein) as well as to be fixed to a top portion of the rail assembly 50 (e.g., to the mount support 167). As shown in FIG. 14, the lower base 186 is positioned substantially below the lower paddle 184 and includes a horizontal extension 188 and at least two vertical extensions 192. Additionally, the lower base 186 vertically spaces apart the lower paddle 184 (and therefore the entire table 110) from the rail assembly 50 in order to allow sufficient room for the shield 30, including the angled end 39 of the shield 30, to pass under the lower paddle 184 (and the entire table 110) while the position of the shield 30 is being adjusted.

As shown in FIGS. 13B-14, the horizontal extension 188 extends horizontally away from the lower paddle 184 in order to reach and attach to the upper base 166 of the upper clamp 162. Accordingly, the horizontal extension 188 includes a hole 185 that extends substantially vertically through the horizontal extension 188 and along the height of the horizontal extension 188. The hole 185 is configured to receive at least a portion of a fastener (e.g., a pin or bolt 189) (and accordingly extends completely through the horizontal extension 188) in order to attach to the upper clamp 162. The horizontal extension 188 is sized to fit within the notch 163 of the upper clamp 162 such that the hole 185 of the lower clamp 182 aligns with the hole 165 on the upper clamp 162 and the side walls and back wall of the upper base 166 extend vertically along the sides of the horizontal extension 188.

In order to attach the upper clamp 162 and the lower clamp 182 together, the notch 163 of the upper clamp 162 and the horizontal extension 188 of the lower clamp 182 are first aligned with each other (as shown in FIG. 14). (It is noted that, although the bolt 189 is shown within the upper clamp 162 in FIG. 14, the bolt 189 may not extend all the way through the upper base 166 until the hole 185 of the lower clamp 182 and the hole 165 on the upper clamp 162 are aligned along their respective longitudinal axes.) The upper clamp 162 is moved such that the horizontal extension 188 of the lower clamp 182 is positioned within the notch 163 of the upper clamp 162, which aligns the hole 185 of the lower clamp 182 with the hole 165 on the upper clamp 162 along their respective longitudinal axes. Depending on the configuration of the upper clamp 162, the bottom surface of the front wall 161 may rest along the top surface of the horizontal extension 188. The bolt 189 is then moved through both the hole 165 on the upper clamp 162 and the hole 185 of the lower clamp 182 and is tightened (with, for example, a wing nut), as shown in FIG. 13B. Tightening the bolt moves the upper clamp 162 and the lower clamp 182 vertically closer to each other according to the specific thickness of the table 110, thereby securing the table 110 between the upper paddle 164 and the lower paddle 184. The table 110 may already be positioned at least on top of the lower paddle 184 of the lower clamp 182 before the bolt 189 is tightened.

Since the upper clamp 162 and the lower clamp 182 can move vertically relative to each other as the upper clamp 162 is being tightened to the lower clamp 182 and thereby tightened to any vertical distance relative to each other, the vertical distance between the upper paddle 164 and the lower paddle 184 may be customized according to the specific thickness of the table 110 the clamp mount 160 is presently being used with. Once the clamp mount 160 is attached to the table 110 and when the radiation shield assembly 20 is being used, a mattress or pad may be laid on the top surface 114 of the table 110 (and therefore directly over the upper paddle 164 of the upper clamp 162), which separates the patient from the upper paddle 164 of the clamp mount 160 and provides an area for the patient lie on. The weight of the patient on the upper paddle 164 also helps keep the clamp mount 160 (and therefore the entire radiation shield assembly 20) securely attached to the table 110 and in place.

In order to prevent misalignment of the upper paddle 164 of the upper clamp 162 and the lower paddle 184 of the lower clamp 182 during use and to guide the movement of the upper base 166 of the upper clamp 162 up and down along the horizontal extension 188 of the lower clamp 182, the lower clamp 182 may include a wedge, lip, or protrusion 198 (e.g., a protruding or elevated surface), as shown in FIG. 14. The lower clamp 182 may include two protrusions 198 positioned along opposite sides of the lower base 186. The protrusion 198 is positioned such that the end or edge of the protrusion 198 directly abuts and opposes the front edge of the upper base 166 (along the notch 163 and below the front wall 161) of the upper clamp 162 (as shown in FIG. 13B), which prevents the upper clamp 162 or the lower clamp 182 from rotating relative to each other when assembled together. Accordingly, the width of the lower clamp 182 along the protrusions 198 is greater than the inner width of the notch 163 and therefore also greater than the width of the horizontal extension 188 (see FIG. 14), which fits within the notch 163. The protrusion 198 may, however, provide a small tolerance to allow the upper clamp 162 slightly rotate relative to the lower clamp 182 to create a small gap between the upper base 166 and the protrusion 198.

Without this protrusion 198, the upper paddle 164 of the upper clamp 162 may become misaligned and angled (i.e., not approximately parallel) relative to the lower paddle 184 of the lower clamp 182 during use, in particular if the edge or portions of the bottom surface 112 or top surface 114 of the table 110 are angled (e.g., portions of the bottom surface 112 that may not be parallel to the top surface 114 of the table 110). For example, the lower clamp 182 may pivot away from the upper clamp 162 as the clamp mount 160 is being tightened to the table 110 such that the ends of the upper paddle 164 and the lower paddle 184 that are closest to the upper base 166 are angled closer to each other (compared to the ends of the upper paddle 164 and the lower paddle 184 that are opposite the upper base 166). However, the protrusions 198 prevent this misalignment.

As shown in FIGS. 13B-14, the vertical extensions 192 extend vertically below the lower paddle 184 (in a substantially perpendicular manner to the lower paddle 184) from a lower surface of the lower base 186 in order to reach and attach to the rail assembly 50, in particular the mount support 167 of the rail assembly 50. As shown, the clamp mount 160 attaches to the two-sided extension 168 (that is one type of mount support 167) in order to attach to both sides of the rail 51 (or the cross-beam 56) for a more secure attachment (and to prevent torque from being applied to the rail 51 (or the cross-beam 56)).

As shown in FIG. 14, the lower clamp 182 includes two sets or pairs of vertical extensions 192 that form both a rail channel 194 and a mount support channel 196. The rail channel 194 and the mount support channel 196 extend substantially perpendicularly to each other (since the rail 51 and the two-sided extension 168 are substantially perpendicular to each other).

The rail slot or channel 194 is formed between the two sets of vertical extensions 192 and is sized and configured to receive a portion of the length of the rail 51 (or the cross-beam 56) of the rail assembly 50 along the width of the rail 51. Accordingly, the rail channel 194 (i.e., the distance between the two sets of vertical extensions 192) is approximately equal to (or slightly larger than) the width of the rail 51 in order to receive the width of the rail 51. The rail channel 194 extends completely through the lower clamp 182. Accordingly, the rail 51 extends within and through the rail channel 194 once the lower clamp 182 is assembled to the rail assembly 50 such that the two sets of vertical extensions 192 are positioned along opposite side walls 49 of the rail 51. The two sets of vertical extensions 192 may be substantially symmetrical about the rail channel 194.

The mount support slot or channel 196 is formed within (and extends through) each of the sets of vertical extensions 192 and is sized and configured to receive the mount support 167 (specifically the two-sided extension 168) along the width of the mount support 167. As shown in FIG. 14, the mount support channel 196 extends completely through the lower clamp 182, continuously through and between the two sets of vertical extensions 192. Accordingly, the two-sided extension 168 is configured to be positioned within the mount support channel 196 such that the two-sided extension 168 extends within and at least partially through the mount support channel 196 once the lower clamp 182 is assembled to the rail assembly 50. The vertical extensions 192 (within each of the sets of vertical extension 192) are thus positioned on opposite sides of the two-sided extension 168. The vertical extensions 192 within each of the sets of vertical extensions 192 may be substantially symmetrical about the mount support channel 196. However, according to another embodiment, the lower clamp 182 may be configured to only include two vertical extensions 192 that form the rail channel 194 therebetween (and thus do not form the mount support channel 196).

Each of the vertical extension 192 includes and defines a hole 193 that extends completely through the vertical extension 192. The holes 193 are configured to receive at least a portion of a fastener (e.g., a pin, screw, or bolt 199) in order to attach to the two-sided extension 168. The holes 193 within each of the vertical extensions 192 within each of the sets of vertical extensions 192 are aligned with each other along their longitudinal axes such that the bolt 199 can extend completely through two vertical extensions 192 within the same set of vertical extensions 192. Each of the sets of vertical extensions 192 are configured to receive a bolt 199 that extends through each of the vertical extensions 192 within the set. Accordingly, with two sets of vertical extension 192, two bolts 199 may be positioned within and extend through a respective hole 193 and a respective base 55 of the two-sided extension 168 on opposite sides of the rail 51 or the cross-beam 56, which allows each of the two bases 55 of the two-sided extension 168 to be attached to opposite sides of the lower clamp 182 once the lower clamp 182 is assembled to the two-sided extension 168.

In order to attach the lower clamp 182 and the two-sided extension 168 together (as shown in FIG. 14), the rail channel 194 is aligned along the width of the rail 51 such that the rail 51 can slide into the rail channel 194, and the mount support channel 196 is aligned along the width of the two-sided extension 168 such that the two-sided extension 168 can slide into the mount support channel 196. The lower clamp 182 is then placed over the two-sided extension 168, thereby aligning the holes 53 of each of the bases 55 of the two-sided extension 168 with the holes 193 through each set of the vertical extensions 192. Bolts 199 can be moved through a hole 193 of one vertical extension 192, subsequently through a hole 53 of one of the bases 55 of the two-sided extensions 168, and then through a hole 193 of another vertical extension 192 within the same set of vertical extensions 192 and subsequently tightened, thereby attaching the lower clamp 182 to the two-sided extension 168 (as shown in FIG. 13B).

The lower clamp 182 may have a variety of different dimensions according to the desired configuration. According to one embodiment, the total length of the entire lower clamp 182 is approximately 7 inches, and the total height of the entire lower clamp 182 is approximately 2.30 inches. The width of the lower paddle 184 (which may be the maximum width of the lower clamp 182) is approximately 2 inches.

The width of the horizontal extension 188 may be approximately 0.90 inches (the horizontal extension 188 may be substantially wide in order to prevent the lower clamp 182 and the upper clamp 162 from pivoting relative to each other). The height of the horizontal extension 188 may be approximately 0.70 inches.

The length of the protrusion 198 is approximately 0.70 inches, the width of the lower clamp 182 along the region with the protrusion 198 is approximately 1.25 inches, and the height of the protrusion 198 is approximately 0.60 inches.

The distance between the outer sides of a set of vertical extensions 192 is approximately 1.2 inches, and the distance between the inner sides of a set of vertical extensions 192 is approximately 0.90 inches. The length of each of the vertical extensions 192 is approximately 0.70 inches, the distance between two sets of vertical extensions 192 (i.e., the width of the rail channel 194) is approximately 0.90 inches, and the width of the lower base 186 along the vertical extensions 192 is approximately 2.30 inches.

In order to accommodate tables 110 of different widths (due to, for example, dimensional differences due to the particular vendor of the table 110), the size of the clamp mount 160 may have a variety of different sizes. For example, the length of the horizontal extensions 188 may be increased from approximately 0.75 inches to 1.75 inches, thus increasing the length of the entire lower clamp 182 from approximately 7 inches to 8 inches and moving the position of the holes 185 of each of the respective horizontal extensions 188 outward. Accordingly, the upper clamp 162 is attached to the lower clamp 182 in a position further outward (relative to a center of the table 110 when assembled). Therefore, instead of securing a table 110 with a width of approximately 17.75-18 inches, the clamp mount 160 can secure to a table 110 with a width of approximately 19.75 inches. The other dimensions and configuration of the clamp mount 160 may remain the same.

Additionally, the table mounts 157 may be attached to tables 110 without a taper (as shown in solid lines FIG. 13B) or with a taper 116 (as shown in dashed lines in FIG. 13B). The taper 116 may be a portion of the table 110 along which the thickness of the table increases or decreases and that is angled relative to the horizontal and vertical axes of the table 110. The tapers 116 may be a variety of different sizes and shapes (i.e., longer or shorter or at a variety of different angles). The taper 116 may extend along the bottom surface 112 of the table 110 along the outer edge of the table 110. Furthermore, the table 110 may have a lip around the outermost edge of the taper 116 that also has a variety of different sizes, according to the desired configuration of the table and, for example only, the brand of the table. The lower paddle 184 (and optionally the upper paddle 164) extends along a substantial portion of the width of the table 110 and therefore extends beyond the inner edge of the taper 116, which allows the clamp mount 160 to securely and stably attach to tables 110 with tapers 116.

The clamp mount 160 may be constructed out of a variety of different materials including, but not limited to, carbon fiber, in order to avoid any interference with the radiation 122.

Radiation Shield Assembly Use and Adjustment

As shown in FIGS. 1-3, the radiation shield assembly 20 is configured to be attached to an examination table 110 in order to shield certain areas of a patient 10 from excess radiation. Accordingly, the table mounts 157 (which may include the clamp mounts 160 and/or the suction mounts 60) are mounted to the table 110 and attached to the rail assembly 50 (in either order). The shield 30 is then movably attached to the rails 51 of the rail assembly 50.

Once the radiation shield assembly 20 is attached to the table 110, the position of the shield 30 relative to the table 110 can be adjusted according to the desired position. For example, FIGS. 1-2 show the shield 30 of the radiation shield assembly 20 being moved from a retracted position 32 (as shown in FIG. 1) to a partially extended position 34 (as shown in FIG. 2). The shield 30 can then be moved to an extended position 36 (as shown in FIG. 4) along at least a portion of the length of the table 110. In order to move the shield 30, the user grasps and at least partially compresses the locking handle 140 and, while still compressing the locking handle 140, moves the shield 30 to the desired location. The user then releases the locking handle 140, which automatically locks the shield 30 into position along the length of the rails 51 (and thereby along the length of the table 110). The shield 30 can be moved from the extended position 36, though partially extended positions 34, and to the retracted position 32 before, during, and after a procedure according to the desired amount and location of radiation shielding, with or without a patient 10 on top of the table 110 (and without disturbing the patient 10 or the sterile area on top of the table 110).

In FIG. 4, the radiation shield assembly is in the extended position 36. Accordingly, if attached to the rest of the radiation shield assembly 20, the shield 30 would be fully extended (and completely unfolded) along the length of the rails 51 of the rail assembly 50 and substantially parallel to the table 110. In the extended position 36, the angled end 39 of the shield 30 may abut the cross-beam 56 at one end of the rail assembly 50. The corner supports 59 of the rail assembly 50 cause the flaps 97 of the shield 30 to curve inwardly and toward the opposite end of the rail assembly 50.

In order to move the shield 30, the user grasps and at least partially compresses the handle 140 (which unlocks the handle 140) and concurrently moves the handle 140 along at least a portion of the length of the rails 51, which moves the shield 30 with the handle 140 along the portion of the length of the rails 51. As the handle 140 is moved, at least a portion of the shield 30 is moved along with the handle 140, and the roller structures 73 move within the rails 51 (as shown and described further herein). Furthermore, the angled end 39 of the shield 30 (near which the handle 140 may be positioned and attached to) is moved away from the end of the rails (e.g., from the cross-beam 56 at the end of the rail assembly 50) when the handle 140 is moved from the extended position 36, thereby exposing a portion of the table 110 (and this end of the rail assembly 50) to radiation 122. The shield 30 can be positioned and locked in a variety of different partially extended positions 34, depending on the desired amount and location of radiation shielding. The user can release the handle 140 anywhere along the length of the rails 51 in order to lock the shield 30 into any particular partially extended position 34 along the length of the rails 51. The angled end 39 of the shield 30 can be moved directly underneath the table mounts 157 (e.g., the clamp mounts 160) due to the vertical space between the shield 30 and the table mount 157 created by the lower base 186 of the lower clamp 182 (as described further herein).

In FIG. 1, the radiation shield assembly 20 is in the retracted position 32. Accordingly, the shield 30 is fully retracted along the length of the rails 51 of the rail assembly 50. In the retracted position 32, the shield 30 may be folded up toward one end of the rails 51 or folded and positioned anywhere along the length of the rails 51. For example, the shield 30 may optionally be folded up toward the suction mounts 60 such that the angled end 39 of the shield 30 abuts the suction mounts 60 and/or the one-sided extension 58 of the rail assembly 50. The shield 30 may optionally be moved underneath and past the table mounts 157 (e.g., the clamp mounts 160 and/or the suction mounts 60) such that the angled end 39 of the shield 30 can be positioned on either side of the table mounts 157.

In order to move the shield 30 from the retracted position 32 back to the extended position 36, the same process can be followed, except moving the handle 140 in the opposite direction along the length of the rails 51.

Experimental Results

In order to access the effectiveness of the radiation shield assembly 20, radiation levels at specific locations were measured during various bench test radiologic procedures, in quasi-lab conditions and with real time radiation detectors to assess the radiation dose at different locations with and without the radiation shield assembly 20. These various experimental procedures and results described herein are for exemplary purposes only and not intended to be limiting in any way.

An acrylic phantom model (developed by American National Standards Institute and the Center for Devices and Radiologic Health (CDRH)) was used in experimentation in order to allow serial measurements with the same parameters. Patient equivalency of the phantom model has been established clinically. (Chu R Y L, Fisher J, Archer B R, et al. *Standardized methods for measuring diagnostic x-ray exposures*. AAPM Report NO. 31 published for the American Association of Physicians in Medicine by the American Institute of Physics, 1990.) Accordingly, an acrylic block was used to simulate the heart of a 160-170 pound patient. The acrylic block has the density of a thoracic cavity (approximately). The acrylic block was 7.87 inches (200 mm) thick, 11.81 inches (30 cm) long, and 11.81 inches wide.

The height of the table 110 was −5.12 inches (−13 cm) below the isocenter. The source image detector (SID) was 39.37 inches (100 cm) and the fluoroscopy was 30 frames per second, with duration of one minute. The projections or camera angles were right anterior oblique (RAO) at 30°, left anterior oblique (LAO) at 30°, and straight anterior posterior (AP).

Multiple Gieger counters or real-time radiation detectors (e.g., RaySafe™) were used to measure the cumulative radiation around the acrylic block in three different configurations (i.e., open, collimation, and radiation pads) with three camera angles (i.e., RAO, LAO, and AP). The radiation detectors were positioned at different locations to measure the radiation 122 exiting the surface of the table 110 (potential exit radiation dose from the table 110 to patient 10 and to the practitioner).

During the experiment, each measurement was taken five times (N=5). Table 1 (below) shows a summary of the measured radiation (in milligray) of each of the radiation detectors at different locations without and with the radiation shield assembly 20. The measured radiation values are shown as the mean±the standard deviation. Table 1 also shows the percent reduction of measured radiation of the experimental setup with the radiation shield assembly 20 compared to the experimental setup without the radiation shield assembly 20. Based on the Kruskal-Wallis test (N=15), significant percentage reductions are designated by * if the p-value is less than 0.01. It is noted that, due to the difference in variability, larger percentages may or may not be statistically significant.

TABLE 1

| Camera Angle | Measured radiation (milligray, without the radiation shield assembly 20) | Measured radiation (milligray, with the radiation shield assembly 20) | Percent Reduction |
|---|---|---|---|
| Patient Right Femoral Artery Area | | | |
| LAO | 0.48 ± .04 | 0.02 ± .04 | 96%* |
| RAO | 1.52 ± .08 | 0.40 ± .01 | 74%* |
| AP | 0.38 ± .04 | 0.06 ± .09 | 84%* |
| Patient Right Hand Area | | | |
| LAO | 25.9 ± .95 | 18.7 ± .57 | 28% |
| RAO | 20.3 ± 1.2 | 12.5 ± .94 | 38% |
| AP | 17.9 ± .19 | 11.3 ± .07 | 37%* |
| Patient Right Mid Thorax | | | |
| LAO | 4.28 ± .22 | 1.40 ± .12 | 67%* |
| RAO | 4.78 ± .33 | 1.54 ± .09 | 68%* |
| AP | 2.74 ± .05 | 0.94 ± .05 | 66%* |
| Right Side Below Table | | | |
| LAO | 90.3 ± 7.9 | 92.5 ± 8.3 | −2% |
| RAO | 31.2 ± 1.8 | 31.2 ± 2.0 | 0% |
| AP | 36.6 ± .40 | 36.1 ± .16 | 1% |
| Patient Groin | | | |
| LAO | 52.1 ± 1.0 | 51.8 ± 2.7 | 1% |
| RAO | 45.5 ± 1.4 | 45.5 ± 1.36 | 0% |
| AP | 47.8 ± .20 | 48.0 ± .42 | 0% |
| Patient Mid Abdomen | | | |
| LAO | 16.6 ± 1.2 | 9.0 ± .78 | 46%* |
| RAO | 13.4 ± .92 | 6.18 ± .61 | 54%* |
| AP | 12.9 ± .12 | 6.9 ± .05 | 47%* |
| Patient Left Femoral Artery Area | | | |
| LAO | 0.78 ± .04 | 0.40 ± .01 | 49%* |
| RAO | 0.50 ± .01 | 0.10 ± .01 | 80%* |
| AP | 0.30 ± .01 | 0.08 ± .08 | 73%* |
| Patient Left Mid Thorax | | | |
| LAO | 27.4 ± 1.7 | 28.0 ± 1.3 | −2% |
| RAO | 73.8 ± 2.5 | 72.7 ± 4.2 | 1% |
| AP | 30.5 ± .30 | 31.0 ± .31 | −2% |

TABLE 1-continued

| Camera Angle | Measured radiation (milligray, without the radiation shield assembly 20) | Measured radiation (milligray, with the radiation shield assembly 20) | Percent Reduction |
|---|---|---|---|
| Patient mGy | | | |
| LAO | 35.8 ± 5.0 | 35.6 ± 4.3 | 1% |
| RAO | 34.8 ± 3.8 | 34.8 ± 4.4 | 0% |
| AP | 19.4 ± .55 | 19.4 ± .55 | 0% |
| Patient mGycm$^2$ | | | |
| LAO | 428.6 ± 49.6 | 436.4 ± 49.1 | −2% |
| RAO | 429.2 ± 49.9 | 428.8 ± 50.8 | 0% |
| AP | 239.8 ± .8 | 239.4 ± 1.5 | 0% |

The results shown in Table 1 show a statistically significant reduction in radiation exposure to the simulated patient (i.e., the acrylic block) and thus to the practitioner. In many locations of the radiation detectors, the radiation exposure is reduced by 60% to 90%. Patient mGy and Patient mGycm$^2$ are controls to show that the power of the x-ray is not increased as a result of including the radiation shield assembly 20.

Additionally, another test was conducted to access the effectiveness of the radiation shield assembly 20 in which the radiation was measured without the radiation shield assembly 20 and with the radiation shield assembly 20, as shown below in Table 2. In particular, radiation levels at various different locations were measured during radiologic procedures with real time radiation detectors to assess the entrance radiation dose 124 (i.e., the amount of radiation that enters into (rather than exits from) the patient) at different locations with and without the radiation shield assembly 20. To measure the entrance radiation dose 124, the radiation detectors were placed on top of the table, measuring the radiation coming out of the table from the radiation source, before going through any patient or patient model.

Table 2 shows the measured amount of radiation that the patient receives at various different locations 1-8. Measurements were taken at three different camera angles (i.e., RAO, LAO, and AP), without and with the radiation shield assembly 20 for comparison. Each of the measurements were taken in open field. The percent reduction of radiation is shown for each measurement.

TABLE 2

| Camera Angle | Measured Radiation (milligray, without the radiation shield assembly 20) | Measured Radiation (milligray, with the radiation shield assembly 20) | Percent Reduction |
|---|---|---|---|
| Location 1 | | | |
| LAO | 0.68 | 0.02 | 97.06% |
| RAO | 0.36 | 0.02 | 94.44% |
| AP | 0.36 | 0 | 100.00% |
| Location 2 | | | |
| LAO | 0.67 | 0.1 | 85.07% |
| RAO | 0.4 | 0.1 | 75.00% |
| AP | 0.4 | 0 | 100.00% |
| Location 3 | | | |
| LAO | 1.63 | 0.2 | 87.73% |
| RAO | 0.7 | 0.18 | 74.29% |
| AP | 0.7 | 0 | 100.00% |
| Location 4 | | | |
| LAO | 2.63 | 0.6 | 77.19% |
| RAO | 3.12 | 0.98 | 68.59% |
| AP | 1.54 | 0.4 | 74.03% |
| Location 5 | | | |
| LAO | 1.73 | 0.2 | 88.44% |
| RAO | 1.24 | 0.26 | 79.03% |
| AP | 0.7 | 0.1 | 85.71% |
| Location 6 | | | |
| LAO | 3.17 | 0.68 | 78.55% |
| RAO | 2.24 | 0.7 | 68.75% |
| AP | 1.5 | 0.4 | 73.33% |
| Location 7 | | | |
| LAO | 2.83 | 0.2 | 92.93% |
| RAO | 1.64 | 0.22 | 86.59% |
| AP | 1.64 | 0.02 | 98.78% |
| Location 8 | | | |
| LAO | 3.62 | 0.8 | 77.90% |
| RAO | 1.48 | 0.42 | 71.62% |
| AP | 1.26 | 0.3 | 76.19% |

As shown, by including the radiation shield assembly 20, the amount of radiation that both the operator (or practitioner) and the patient are exposed is reduced to compared to the amount of radiation that the operator and the patient are exposed to without the radiation shield assembly 20.

It is understood that the various dimensions and sizes of the components of the radiation shield assembly 20 are exemplary only and may be changed according to the desired configuration.

The embodiments disclosed herein provide a radiation shield assembly. Besides those embodiments depicted in the figures and described in the above description, other embodiments of the present invention are also contemplated. For example, any single feature of one embodiment of the present invention may be used in any other embodiment of the present invention.

Given the disclosure of the present invention, one versed in the art would appreciate that there may be other embodiments and modifications within the scope and spirit of the invention. Accordingly, all modifications attainable by one versed in the art from the present invention within the scope and spirit of the present invention are to be included as further embodiments of the present invention.

What is claimed is:

1. A radiation shield assembly comprising:
   a shield configured to attenuate radiation; and
   a shield supporting assembly configured to position the shield in between a patient support and a radiation source and to support the shield such that the shield extends across at least a portion of the width of the patient support,
   wherein the shield is movable between a retracted position and an extended position along a length of the shield supporting assembly,
   wherein, in the extended position, the shield extends along a portion of the patient support and attenuates radiation from the radiation source to the portion of the patient support,
   wherein, in the retracted position, the shield exposes at least some of the portion of the patient support to the radiation.

2. The radiation shield assembly of claim 1, wherein the shield supporting assembly is configured to position the shield below the patient support and above the radiation source.

3. The radiation shield assembly of claim 1, wherein the shield is movable between the retracted position and the extended position while a patient is laying on the patient support.

4. The radiation shield assembly of claim 1, wherein the shield supporting assembly does not block or materially affect radiation.

5. The radiation shield assembly of claim 1, further comprising at least one mount configured to removably and reattachably attach the shield supporting assembly to the patient support without any modifications to the patient support.

6. The radiation shield assembly of claim 5, wherein the at least one mount is a clamp mount configured to clamp a top surface and a bottom surface of the patient support.

7. The radiation shield assembly of claim 5, wherein the shield supporting assembly comprises at least one rail and at least one mount support that extends perpendicularly from the at least one rail, wherein the at least one mount is configured to attach to the mount support.

8. The radiation shield assembly of claim 7, wherein the at least one mount support is a two-sided extension that extends from opposite sides of the at least one rail.

9. The radiation shield assembly of claim 7, wherein the at least one mount support is a one-sided extension that extends from one side of the at least one rail.

10. The radiation shield assembly of claim 1, further comprising a locking mechanism configured to lock the shield in the retracted position, in the extended position, or in a position between the retracted position and the extended position.

11. The radiation shield assembly of claim 10, wherein the locking mechanism is a locking handle that is configured to be moved between a locked position and an unlocked position.

12. The radiation shield assembly of claim 1, further comprising a plurality of shield supports that are configured to support the shield and fold the shield in the retracted position.

13. The radiation shield assembly of claim 12, wherein the plurality of shield supports comprises at least one rod and at least one bar.

14. The radiation shield assembly of claim 1, wherein the shield comprises at least one angled end that extends substantially perpendicular from a body of the shield when the shield is in the extended position.

15. The radiation shield assembly of claim 14, further comprising a deflector that angles and supports the at least one angled end of the shield relative to the body of the shield.

16. The radiation shield assembly of claim 14, wherein the angled end comprises at least one flap that moves independently in the direction of movement of the shield along the shield supporting assembly relative to the rest of the angled end and the body of the shield.

17. The radiation shield assembly of claim 1, further comprising a plurality of shield adjusters attached to the shield and configured to allow the shield to move along the length of the shield supporting assembly.

18. The radiation shield assembly of claim 17, wherein the shield supporting assembly comprises at least one rail that extends along the length of the shield supporting assembly and comprises a slot, wherein a portion of each of the plurality of shield adjusters is configured to move within and along the slot of the at least one rail.

19. The radiation shield assembly of claim 18, wherein the plurality of shield adjusters each comprise a roller structure that is configured to roll within the slot and a fastener that is configured to attach the roller structure and the shield together.

20. A radiation shield assembly comprising:
a shield configured to attenuate radiation;
a shield supporting assembly configured to position the shield in between a patient support and a radiation source,
wherein the shield is movable between a retracted position and an extended position along a length of the shield supporting assembly,
wherein, in the extended position, the shield extends along a portion of the patient support and attenuates radiation from the radiation source to the portion of the patient support,
wherein, in the retracted position, the shield exposes at least some of the portion of the patient support to the radiation; and
at least one mount configured to removably and reattachably attach the shield supporting assembly to the patient support without any modifications to the patient support,
wherein the at least one mount is configured to removably and reattachably attach to a bottom surface of the patient support such that the shield and the shield supporting assembly are positioned along the bottom surface of the patient support.

* * * * *